(12) United States Patent
Quanci et al.

(10) Patent No.: US 12,190,701 B2
(45) Date of Patent: * Jan. 7, 2025

(54) METHODS AND SYSTEMS FOR AUTOMATICALLY GENERATING A REMEDIAL ACTION IN AN INDUSTRIAL FACILITY

(71) Applicant: SUNCOKE TECHNOLOGY AND DEVELOPMENT LLC, Lisle, IL (US)

(72) Inventors: John Francis Quanci, Haddonfield, NJ (US); Andre Vassilnenko Kalinin, Jardim Limoelro (BR)

(73) Assignee: SUNCOKE TECHNOLOGY AND DEVELOPMENT LLC, Lisle, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/047,916

(22) Filed: Oct. 19, 2022

(65) Prior Publication Data
US 2023/0360511 A1    Nov. 9, 2023

Related U.S. Application Data

(63) Continuation of application No. 15/614,525, filed on Jun. 5, 2017, now Pat. No. 11,508,230.
(Continued)

(51) Int. Cl.
*G08B 21/16* (2006.01)
*B01D 53/30* (2006.01)
(Continued)

(52) U.S. Cl.
CPC ......... *G08B 21/16* (2013.01); *F02D 41/1441* (2013.01); *G01N 33/0032* (2013.01);
(Continued)

(58) Field of Classification Search
None
See application file for complete search history.

(56) References Cited

U.S. PATENT DOCUMENTS

| 425,797 A | 4/1890 | Hunt |
| 469,868 A | 3/1892 | Osbourn |

(Continued)

FOREIGN PATENT DOCUMENTS

| CA | 1172895 | 8/1984 |
| CA | 2775992 | 5/2011 |

(Continued)

OTHER PUBLICATIONS

U.S. Appl. No. 09/783,195, filed Feb. 14, 2001, now U.S. Patent No. 6,596, 128, titled Coke Oven Flue Gas Sharing.
(Continued)

*Primary Examiner* — Sean Shechtman
(74) *Attorney, Agent, or Firm* — Perkins Coie LLP

(57) ABSTRACT

Systems and methods of preventing an event occurrence or mitigating effects of an event occurrence in an industrial facility are disclosed herein. In some embodiments, a first input is received from a first sensor and, based at least in part on the first input, an initial action is automatically generated. In response to the initial action, a second input is received from a second sensor and, based at least in part of the received first and second inputs, a likelihood of an event occurrence is determined. Based at least in part of the determined likelihood, a remedial action configured to prevent the occurrence of the event occurrence is automatically generated. In some embodiments, the remedial action is generated in real-time and can be directed to a process condition, environmental condition, or secondary source.

10 Claims, 11 Drawing Sheets

Related U.S. Application Data

(60) Provisional application No. 62/345,717, filed on Jun. 3, 2016.

(51) Int. Cl.
  *C01B 17/69* (2006.01)
  *C01B 21/24* (2006.01)
  *C01B 21/36* (2006.01)
  *C08K 5/37* (2006.01)
  *F02D 41/14* (2006.01)
  *G01N 33/00* (2006.01)
  *G05B 19/418* (2006.01)
  *G05B 23/02* (2006.01)
  *G08B 3/10* (2006.01)
  *G08B 5/36* (2006.01)

(52) U.S. Cl.
  CPC ....... *G05B 19/418* (2013.01); *G05B 23/0235* (2013.01); *G05B 23/0283* (2013.01); *G08B 3/10* (2013.01); *G08B 5/36* (2013.01); *B01D 53/30* (2013.01); *B01D 2251/104* (2013.01); *B01D 2251/2062* (2013.01); *B01D 2251/208* (2013.01); *B01D 2251/21* (2013.01); *B01D 2251/502* (2013.01); *B01D 2251/508* (2013.01); *B01D 2251/51* (2013.01); *C01B 17/69* (2013.01); *C01B 21/24* (2013.01); *C01B 21/36* (2013.01); *C08K 5/37* (2013.01)

(56) References Cited

U.S. PATENT DOCUMENTS

| | | |
|---|---|---|
| 705,926 A | 7/1902 | Hemingway |
| 760,372 A | 5/1904 | Beam |
| 845,719 A | 2/1907 | Schniewind |
| 875,989 A | 1/1908 | Garner |
| 976,580 A | 7/1909 | Krause |
| 1,140,798 A | 5/1915 | Carpenter |
| 1,424,777 A | 8/1922 | Schondeling |
| 1,430,027 A | 9/1922 | Plantinga |
| 1,486,401 A | 3/1924 | Van Ackeren |
| 1,530,995 A | 3/1925 | Geiger |
| 1,572,391 A | 2/1926 | Klaiber |
| 1,677,973 A | 7/1928 | Marquard |
| 1,705,039 A | 3/1929 | Thornhill |
| 1,721,813 A | 7/1929 | Geipert |
| 1,757,682 A | 5/1930 | Palm |
| 1,818,370 A | 8/1931 | Wine |
| 1,818,994 A | 8/1931 | Kreisinger |
| 1,830,951 A | 11/1931 | Lovett |
| 1,848,818 A | 3/1932 | Becker |
| 1,895,202 A | 1/1933 | Montgomery |
| 1,947,499 A | 2/1934 | Schrader et al. |
| 1,955,962 A | 4/1934 | Jones |
| 1,979,507 A | 11/1934 | Underwood |
| 2,075,337 A | 3/1937 | Burnaugh |
| 2,141,035 A | 12/1938 | Daniels |
| 2,195,466 A | 4/1940 | Otto |
| 2,235,970 A | 3/1941 | Wilputte |
| 2,340,283 A | 1/1944 | Vladu |
| 2,340,981 A | 2/1944 | Otto |
| 2,343,034 A | 2/1944 | Weber |
| 2,394,173 A | 2/1946 | Harris et al. |
| 2,424,012 A | 7/1947 | Bangham et al. |
| 2,486,199 A | 10/1949 | Nier |
| 2,609,948 A | 9/1952 | Laveley |
| 2,641,575 A | 6/1953 | Otto |
| 2,649,978 A | 8/1953 | Smith |
| 2,667,185 A | 1/1954 | Beavers |
| 2,723,725 A | 11/1955 | Keiffer |
| 2,756,842 A | 7/1956 | Chamberlin et al. |
| 2,765,266 A | 10/1956 | Throop et al. |
| 2,813,708 A | 11/1957 | Frey |
| 2,827,424 A | 3/1958 | Homan |
| 2,873,816 A | 2/1959 | Emil et al. |
| 2,902,991 A | 9/1959 | Whitman |
| 2,907,698 A | 10/1959 | Schulz |
| 2,968,083 A | 1/1961 | Lentz et al. |
| 3,010,882 A | 11/1961 | Barclay et al. |
| 3,015,893 A | 1/1962 | McCreary |
| 3,026,715 A | 3/1962 | Briggs |
| 3,033,764 A | 5/1962 | Hannes |
| 3,085,582 A | 4/1963 | Slosman |
| 3,175,961 A | 3/1965 | Samson |
| 3,199,135 A | 8/1965 | Trucker |
| 3,224,805 A | 12/1965 | Clyatt |
| 3,259,551 A | 7/1966 | Thompson, Jr. |
| 3,265,044 A | 8/1966 | Juchtern |
| 3,267,913 A | 8/1966 | Jakob |
| 3,327,521 A | 6/1967 | Briggs |
| 3,342,990 A | 9/1967 | Barrington et al. |
| 3,444,046 A | 5/1969 | Harlow |
| 3,444,047 A | 5/1969 | Wilde |
| 3,448,012 A | 6/1969 | Allred |
| 3,453,839 A | 7/1969 | Sabin |
| 3,462,345 A | 8/1969 | Kernan |
| 3,462,346 A | 8/1969 | Kernan et al. |
| 3,511,030 A | 5/1970 | Brown et al. |
| 3,542,650 A | 11/1970 | Kulakov |
| 3,545,470 A | 12/1970 | Paton |
| 3,587,198 A | 6/1971 | Hensel |
| 3,591,827 A | 7/1971 | Hall |
| 3,592,742 A | 7/1971 | Thompson |
| 3,616,408 A | 10/1971 | Hickam |
| 3,623,511 A | 11/1971 | Levin |
| 3,630,852 A | 12/1971 | Nashan et al. |
| 3,652,403 A | 3/1972 | Knappstein et al. |
| 3,676,305 A | 7/1972 | Cremer |
| 3,709,794 A | 1/1973 | Kinzler et al. |
| 3,710,551 A | 1/1973 | Sved |
| 3,746,626 A | 7/1973 | Morrison, Jr. |
| 3,748,235 A | 7/1973 | Pries |
| 3,784,034 A | 1/1974 | Thompson |
| 3,806,032 A | 4/1974 | Pries |
| 3,811,572 A | 5/1974 | Tatterson |
| 3,836,161 A | 10/1974 | Pries |
| 3,839,156 A | 10/1974 | Jakobi et al. |
| 3,844,900 A | 10/1974 | Schulte |
| 3,857,758 A | 12/1974 | Mole |
| 3,875,016 A | 4/1975 | Schmidt-Balve |
| 3,876,143 A | 4/1975 | Rossow et al. |
| 3,876,506 A | 4/1975 | Dix et al. |
| 3,878,053 A | 4/1975 | Hyde |
| 3,894,302 A | 7/1975 | Lasater |
| 3,897,312 A | 7/1975 | Armour et al. |
| 3,906,992 A | 9/1975 | Leach |
| 3,912,091 A | 10/1975 | Thompson |
| 3,912,597 A | 10/1975 | MacDonald |
| 3,917,458 A | 11/1975 | Polak |
| 3,928,144 A | 12/1975 | Jakimowicz |
| 3,930,961 A | 1/1976 | Sustarsic et al. |
| 3,933,443 A | 1/1976 | Lohrmann |
| 3,957,591 A | 5/1976 | Riecker |
| 3,959,084 A | 5/1976 | Price |
| 3,963,582 A | 6/1976 | Helm et al. |
| 3,969,191 A | 7/1976 | Bollenbach |
| 3,975,148 A | 8/1976 | Fukuda et al. |
| 3,979,870 A | 9/1976 | Moore |
| 3,984,289 A | 10/1976 | Sustarsic et al. |
| 3,990,948 A | 11/1976 | Lindgren |
| 4,004,702 A | 1/1977 | Szendroi |
| 4,004,983 A | 1/1977 | Pries |
| 4,025,395 A | 5/1977 | Ekholm et al. |
| 4,040,910 A | 8/1977 | Knappstein et al. |
| 4,045,056 A | 8/1977 | Kandakov et al. |
| 4,045,299 A | 8/1977 | McDonald |
| 4,059,885 A | 11/1977 | Oldengott |
| 4,065,059 A | 12/1977 | Jablin |
| 4,067,462 A | 1/1978 | Thompson |
| 4,077,848 A | 3/1978 | Grainer et al. |
| 4,083,753 A | 4/1978 | Rogers et al. |
| 4,086,231 A | 4/1978 | Ikio |
| 4,093,245 A | 6/1978 | Connor |

(56) References Cited

U.S. PATENT DOCUMENTS

| | | |
|---|---|---|
| 4,100,033 A | 7/1978 | Holter |
| 4,100,491 A | 7/1978 | Newman, Jr. et al. |
| 4,100,889 A | 7/1978 | Chayes |
| 4,111,757 A | 9/1978 | Carimboli |
| 4,124,450 A | 11/1978 | MacDonald |
| 4,133,720 A | 1/1979 | Franzer et al. |
| 4,135,948 A | 1/1979 | Mertens et al. |
| 4,141,796 A | 2/1979 | Clark et al. |
| 4,143,104 A | 3/1979 | van Konijnenburg et al. |
| 4,145,195 A | 3/1979 | Knappstein et al. |
| 4,147,230 A | 4/1979 | Ormond et al. |
| 4,162,546 A | 7/1979 | Shortell et al. |
| 4,176,013 A | 11/1979 | Garthus et al. |
| 4,181,459 A | 1/1980 | Price |
| 4,189,272 A | 2/1980 | Gregor et al. |
| 4,194,951 A | 3/1980 | Pries |
| 4,196,053 A | 4/1980 | Grohmann |
| 4,211,608 A | 7/1980 | Kwasnoski et al. |
| 4,211,611 A | 7/1980 | Bocsanczy |
| 4,213,489 A | 7/1980 | Cain |
| 4,213,828 A | 7/1980 | Calderon |
| 4,222,748 A | 9/1980 | Argo et al. |
| 4,222,824 A | 9/1980 | Flockenhaus et al. |
| 4,224,109 A | 9/1980 | Flockenhaus et al. |
| 4,225,393 A | 9/1980 | Gregor et al. |
| 4,226,113 A | 10/1980 | Pelletier et al. |
| 4,230,498 A | 10/1980 | Ruecki |
| 4,235,830 A | 11/1980 | Bennett et al. |
| 4,239,602 A | 12/1980 | La Bate |
| 4,248,671 A | 2/1981 | Belding |
| 4,249,997 A | 2/1981 | Schmitz |
| 4,263,099 A | 4/1981 | Porter |
| 4,268,360 A | 5/1981 | Tsuzuki et al. |
| 4,271,814 A | 6/1981 | Lister |
| 4,284,478 A | 8/1981 | Brommel |
| 4,285,772 A | 8/1981 | Kress |
| 4,287,024 A | 9/1981 | Thompson |
| 4,289,479 A | 9/1981 | Johnson |
| 4,289,584 A | 9/1981 | Chuss et al. |
| 4,289,585 A | 9/1981 | Wagener et al. |
| 4,296,938 A | 10/1981 | Offermann et al. |
| 4,298,497 A | 11/1981 | Colombo |
| 4,299,666 A | 11/1981 | Ostmann |
| 4,302,935 A | 12/1981 | Cousimano |
| 4,303,615 A | 12/1981 | Jarmell et al. |
| 4,307,673 A | 12/1981 | Caughey |
| 4,314,787 A | 2/1982 | Kwasnik et al. |
| 4,316,435 A | 2/1982 | Nagamatsu et al. |
| 4,324,568 A | 4/1982 | Wilcox et al. |
| 4,330,372 A | 5/1982 | Cairns et al. |
| 4,334,963 A | 6/1982 | Stog |
| 4,336,107 A | 6/1982 | Irwin |
| 4,336,843 A | 6/1982 | Petty |
| 4,340,445 A | 7/1982 | Kucher et al. |
| 4,342,195 A | 8/1982 | Lo |
| 4,344,820 A | 8/1982 | Thompson |
| 4,344,822 A | 8/1982 | Schwartz et al. |
| 4,353,189 A | 10/1982 | Thiersch et al. |
| 4,366,029 A | 12/1982 | Bixby et al. |
| 4,373,244 A | 2/1983 | Mertens et al. |
| 4,375,388 A | 3/1983 | Hara et al. |
| 4,385,962 A | 5/1983 | Stewen et al. |
| 4,391,674 A | 7/1983 | Velmin et al. |
| 4,392,824 A | 7/1983 | Struck et al. |
| 4,394,217 A | 7/1983 | Holz et al. |
| 4,395,269 A | 7/1983 | Schuler |
| 4,396,394 A | 8/1983 | Li et al. |
| 4,396,461 A | 8/1983 | Neubaum et al. |
| 4,406,619 A | 9/1983 | Oldengott |
| 4,407,237 A | 10/1983 | Merritt |
| 4,421,070 A | 12/1983 | Sullivan |
| 4,431,484 A | 2/1984 | Weber et al. |
| 4,439,277 A | 3/1984 | Dix |
| 4,440,098 A | 4/1984 | Adams |
| 4,441,892 A | 4/1984 | Schuster |
| 4,445,977 A | 5/1984 | Husher |
| 4,446,018 A | 5/1984 | Cerwick |
| 4,448,541 A | 5/1984 | Lucas |
| 4,452,749 A | 6/1984 | Kolvek et al. |
| 4,459,103 A | 7/1984 | Gieskieng |
| 4,469,446 A | 9/1984 | Goodboy |
| 4,474,344 A | 10/1984 | Bennett |
| 4,487,137 A | 12/1984 | Horvat et al. |
| 4,498,786 A | 2/1985 | Ruscheweyh |
| 4,506,025 A | 3/1985 | Kleeb et al. |
| 4,508,539 A | 4/1985 | Nakai |
| 4,518,461 A | 5/1985 | Gelfand |
| 4,527,488 A | 7/1985 | Lindgren |
| 4,564,420 A | 1/1986 | Spindeler et al. |
| 4,568,424 A | 2/1986 | Bauer |
| 4,568,426 A | 2/1986 | Orlando |
| 4,570,670 A | 2/1986 | Johnson |
| 4,614,567 A | 9/1986 | Stahlherm et al. |
| 4,643,327 A | 2/1987 | Campbell |
| 4,645,513 A | 2/1987 | Kubota et al. |
| 4,655,193 A | 4/1987 | Blacket |
| 4,655,804 A | 4/1987 | Kercheval et al. |
| 4,666,675 A | 5/1987 | Parker et al. |
| 4,680,167 A | 7/1987 | Orlando |
| 4,690,689 A | 9/1987 | Malcosky et al. |
| 4,704,195 A | 11/1987 | Janicka et al. |
| 4,720,262 A | 1/1988 | Durr et al. |
| 4,724,976 A | 2/1988 | Lee |
| 4,726,465 A | 2/1988 | Kwasnik et al. |
| 4,732,652 A | 3/1988 | Durselen et al. |
| 4,749,446 A | 6/1988 | van Laar et al. |
| 4,793,981 A | 12/1988 | Doyle et al. |
| 4,821,473 A | 4/1989 | Cowell |
| 4,824,614 A | 4/1989 | Jones et al. |
| 4,889,698 A | 12/1989 | Moller et al. |
| 4,898,021 A | 2/1990 | Weaver et al. |
| 4,918,975 A | 4/1990 | Voss |
| 4,919,170 A | 4/1990 | Kallinich et al. |
| 4,929,179 A | 5/1990 | Breidenbach et al. |
| 4,941,824 A | 7/1990 | Holter et al. |
| 5,013,408 A | 5/1991 | Asai et al. |
| 5,052,922 A | 10/1991 | Stokman et al. |
| 5,062,925 A | 11/1991 | Durselen et al. |
| 5,078,822 A | 1/1992 | Hodges et al. |
| 5,087,328 A | 2/1992 | Wegerer et al. |
| 5,114,542 A | 5/1992 | Childress et al. |
| 5,213,138 A | 5/1993 | Presz |
| 5,227,106 A | 7/1993 | Kolvek |
| 5,228,955 A | 7/1993 | Westbrook, III |
| 5,234,601 A | 8/1993 | Janke et al. |
| 5,318,671 A | 6/1994 | Pruitt |
| 5,370,218 A | 12/1994 | Johnson et al. |
| 5,398,543 A | 3/1995 | Fukushima et al. |
| 5,423,152 A | 6/1995 | Kolvek |
| 5,447,606 A | 9/1995 | Pruitt |
| 5,480,594 A | 1/1996 | Wilkerson et al. |
| 5,542,650 A | 8/1996 | Abel et al. |
| 5,597,452 A | 1/1997 | Hippe et al. |
| 5,603,810 A | 2/1997 | Michler |
| 5,622,280 A | 4/1997 | Mays et al. |
| 5,659,110 A | 8/1997 | Herden et al. |
| 5,670,025 A | 9/1997 | Baird |
| 5,687,768 A | 11/1997 | Albrecht et al. |
| 5,705,037 A | 1/1998 | Reinke et al. |
| 5,715,962 A | 2/1998 | McDonnell |
| 5,720,855 A | 2/1998 | Baird |
| 5,745,969 A | 5/1998 | Yamada et al. |
| 5,752,548 A | 5/1998 | Matsumoto et al. |
| 5,752,993 A | 5/1998 | Eatough et al. |
| 5,787,821 A | 8/1998 | Bhat et al. |
| 5,810,032 A | 9/1998 | Hong et al. |
| 5,816,210 A | 10/1998 | Yamaguchi |
| 5,857,308 A | 1/1999 | Dismore et al. |
| 5,881,551 A | 3/1999 | Dang |
| 5,913,448 A | 6/1999 | Mann et al. |
| 5,928,476 A | 7/1999 | Daniels |
| 5,966,886 A | 10/1999 | Di Loreto |
| 5,968,320 A | 10/1999 | Sprague |
| 6,002,993 A | 12/1999 | Naito et al. |

(56) References Cited

U.S. PATENT DOCUMENTS

| | | |
|---|---|---|
| 6,003,706 A | 12/1999 | Rosen |
| 6,017,214 A | 1/2000 | Sturgulewski |
| 6,022,112 A | 2/2000 | Isler et al. |
| 6,059,932 A | 5/2000 | Sturgulewski |
| 6,126,910 A | 10/2000 | Wilhelm et al. |
| 6,139,692 A | 10/2000 | Tamura et al. |
| 6,152,668 A | 11/2000 | Knoch |
| 6,156,688 A | 12/2000 | Ando et al. |
| 6,173,679 B1 | 1/2001 | Bruckner et al. |
| 6,187,148 B1 | 2/2001 | Sturgulewski |
| 6,189,819 B1 | 2/2001 | Racine |
| 6,290,494 B1 | 9/2001 | Barkdoll |
| 6,412,221 B1 | 7/2002 | Emsbo |
| 6,424,457 B1 | 7/2002 | Koonmen et al. |
| 6,495,268 B1 | 12/2002 | Harth, III et al. |
| 6,539,602 B1 | 4/2003 | Ozawa et al. |
| 6,596,128 B2 | 7/2003 | Westbrook |
| 6,626,984 B1 | 9/2003 | Taylor |
| 6,699,035 B2 | 3/2004 | Brooker |
| 6,712,576 B2 | 3/2004 | Skarzenski et al. |
| 6,758,875 B2 | 7/2004 | Reid et al. |
| 6,786,941 B2 | 9/2004 | Reeves et al. |
| 6,830,660 B1 | 12/2004 | Yamauchi et al. |
| 6,907,895 B2 | 6/2005 | Johnson et al. |
| 6,946,011 B2 | 9/2005 | Snyder |
| 6,964,236 B2 | 11/2005 | Schucker |
| 7,056,390 B2 | 6/2006 | Fratello |
| 7,077,892 B2 | 7/2006 | Lee |
| 7,314,060 B2 | 1/2008 | Chen et al. |
| 7,331,298 B2 | 2/2008 | Barkdoll et al. |
| 7,433,743 B2 | 10/2008 | Pistikopoulos et al. |
| 7,497,930 B2 | 3/2009 | Barkdoll et al. |
| 7,547,377 B2 | 6/2009 | Inamasu et al. |
| 7,611,609 B1 | 11/2009 | Valia et al. |
| 7,644,711 B2 | 1/2010 | Creel |
| 7,722,843 B1 | 5/2010 | Srinivasachar |
| 7,727,307 B2 | 6/2010 | Winkler |
| 7,785,447 B2 | 8/2010 | Eatough et al. |
| 7,803,627 B2 | 9/2010 | Hodges et al. |
| 7,823,401 B2 | 11/2010 | Takeuchi et al. |
| 7,827,689 B2 | 11/2010 | Crane |
| 7,998,316 B2 | 8/2011 | Barkdoll |
| 8,071,060 B2 | 12/2011 | Ukai et al. |
| 8,079,751 B2 | 12/2011 | Kapila et al. |
| 8,080,088 B1 | 12/2011 | Srinivasachar |
| 8,146,376 B1 | 4/2012 | Williams et al. |
| 8,152,970 B2 | 4/2012 | Barkdoll et al. |
| 8,172,930 B2 | 5/2012 | Barkdoll |
| 8,236,142 B2 | 8/2012 | Westbrook |
| 8,266,853 B2 | 9/2012 | Bloom et al. |
| 8,311,777 B2 | 11/2012 | Suguira et al. |
| 8,383,055 B2 | 2/2013 | Palmer |
| 8,398,935 B2 | 3/2013 | Howell et al. |
| 8,409,405 B2 | 4/2013 | Kim et al. |
| 8,500,881 B2 | 8/2013 | Orita et al. |
| 8,515,508 B2 | 8/2013 | Kawamura et al. |
| 8,568,568 B2 | 10/2013 | Schuecker et al. |
| 8,640,635 B2 | 2/2014 | Bloom et al. |
| 8,647,476 B2 | 2/2014 | Kim et al. |
| 8,800,795 B2 | 8/2014 | Hwang |
| 8,956,995 B2 | 2/2015 | Masasugu et al. |
| 8,980,063 B2 | 3/2015 | Kim et al. |
| 9,039,869 B2 | 5/2015 | Kim et al. |
| 9,057,023 B2 | 6/2015 | Reichelt et al. |
| 9,103,234 B2 | 8/2015 | Gu et al. |
| 9,169,439 B2 | 10/2015 | Sarpen et al. |
| 9,193,913 B2 | 11/2015 | Quanci et al. |
| 9,193,915 B2 | 11/2015 | West et al. |
| 9,200,225 B2 | 12/2015 | Barkdoll et al. |
| 9,238,778 B2 | 1/2016 | Quanci et al. |
| 9,243,186 B2 | 1/2016 | Quanci et al. |
| 9,249,357 B2 | 2/2016 | Quanci et al. |
| 9,273,249 B2 | 3/2016 | Quanci et al. |
| 9,273,250 B2 | 3/2016 | Choi et al. |
| 9,321,965 B2 | 4/2016 | Barkdoll |
| 9,359,554 B2 | 6/2016 | Quanci et al. |
| 9,404,043 B2 | 8/2016 | Kim |
| 9,463,980 B2 | 10/2016 | Fukada et al. |
| 9,476,547 B2 | 10/2016 | Quanci et al. |
| 9,498,786 B2 | 11/2016 | Pearson |
| 9,580,656 B2 | 2/2017 | Quanci et al. |
| 9,672,499 B2 | 6/2017 | Quanci et al. |
| 9,683,740 B2 | 6/2017 | Rodgers et al. |
| 9,708,542 B2 | 7/2017 | Quanci et al. |
| 9,862,888 B2 | 1/2018 | Quanci et al. |
| 9,976,089 B2 | 5/2018 | Quanci et al. |
| 10,016,714 B2 | 7/2018 | Quanci et al. |
| 10,041,002 B2 | 8/2018 | Quanci et al. |
| 10,047,295 B2 | 8/2018 | Chun et al. |
| 10,047,296 B2 | 8/2018 | Chun et al. |
| 10,053,627 B2 | 8/2018 | Sarpen et al. |
| 10,233,392 B2 | 3/2019 | Quanci et al. |
| 10,308,876 B2 | 6/2019 | Quanci et al. |
| 10,323,192 B2 | 6/2019 | Quanci et al. |
| 10,392,563 B2 | 8/2019 | Kim et al. |
| 10,435,042 B1 | 10/2019 | Weymouth |
| 10,526,541 B2 | 1/2020 | West et al. |
| 10,526,542 B2 | 1/2020 | Quanci et al. |
| 10,578,521 B1 | 3/2020 | Dinakaran et al. |
| 10,611,965 B2 | 4/2020 | Quanci et al. |
| 10,619,101 B2 | 4/2020 | Quanci et al. |
| 10,732,621 B2 | 8/2020 | Cella et al. |
| 10,760,002 B2 | 9/2020 | Ball et al. |
| 10,851,306 B2 | 12/2020 | Crum et al. |
| 10,877,007 B2 | 12/2020 | Steele et al. |
| 10,883,051 B2 | 1/2021 | Quanci et al. |
| 10,920,148 B2 | 2/2021 | Quanci et al. |
| 10,927,303 B2 | 2/2021 | Choi et al. |
| 10,947,455 B2 | 3/2021 | Quanci et al. |
| 10,968,393 B2 | 4/2021 | West et al. |
| 10,968,395 B2 | 4/2021 | Quanci et al. |
| 10,975,309 B2 | 4/2021 | Quanci et al. |
| 10,975,310 B2 | 4/2021 | Quanci et al. |
| 10,975,311 B2 | 4/2021 | Quanci et al. |
| 1,378,782 A1 | 5/2021 | Floyd |
| 11,008,517 B2 | 5/2021 | Chun et al. |
| 11,008,518 B2 | 5/2021 | Quanci et al. |
| 11,021,655 B2 | 6/2021 | Quanci et al. |
| 11,053,444 B2 | 7/2021 | Quanci et al. |
| 11,060,032 B2 | 7/2021 | Quanci et al. |
| 11,071,935 B2 | 7/2021 | Quanci et al. |
| 11,098,252 B2 | 8/2021 | Quanci et al. |
| 11,117,087 B2 | 9/2021 | Quanci |
| 11,142,699 B2 | 10/2021 | West et al. |
| 11,186,778 B2 | 11/2021 | Crum et al. |
| 11,193,069 B2 | 12/2021 | Quanci et al. |
| 11,214,739 B2 | 1/2022 | Quanci et al. |
| 11,261,381 B2 | 3/2022 | Quanci et al. |
| 11,359,145 B2 | 6/2022 | Ball et al. |
| 11,359,146 B2 | 6/2022 | Quanci et al. |
| 11,365,355 B2 | 6/2022 | Quanci et al. |
| 11,395,989 B2 | 7/2022 | Quanci et al. |
| 1,429,346 A1 | 9/2022 | Horn |
| 11,441,077 B2 | 9/2022 | Quanci et al. |
| 11,441,078 B2 | 9/2022 | Quanci et al. |
| 11,486,572 B2 | 11/2022 | Quanci et al. |
| 11,505,747 B2 | 11/2022 | Quanci et al. |
| 11,508,230 B2 * | 11/2022 | Quanci .................. G08B 5/36 |
| 11,597,881 B2 | 3/2023 | Quanci et al. |
| 11,643,602 B2 | 5/2023 | Quanci et al. |
| 11,680,208 B2 | 6/2023 | Quanci et al. |
| 11,692,138 B2 | 7/2023 | Quanci et al. |
| 2002/0170605 A1 | 11/2002 | Shiraishi et al. |
| 2003/0014954 A1 | 1/2003 | Ronning et al. |
| 2003/0015809 A1 | 1/2003 | Carson |
| 2003/0057083 A1 | 3/2003 | Eatough et al. |
| 2004/0016377 A1 | 1/2004 | Johnson et al. |
| 2004/0220840 A1 | 11/2004 | Bonissone et al. |
| 2005/0087767 A1 | 4/2005 | Fitzgerald et al. |
| 2005/0096759 A1 | 5/2005 | Benjamine et al. |
| 2006/0029532 A1 | 2/2006 | Breen et al. |
| 2006/0102420 A1 | 5/2006 | Huber et al. |
| 2006/0149407 A1 | 7/2006 | Markham et al. |
| 2007/0087946 A1 | 4/2007 | Quest et al. |

(56) References Cited

U.S. PATENT DOCUMENTS

| | | |
|---|---|---|
| 2007/0102278 A1 | 5/2007 | Inamasu et al. |
| 2007/0116619 A1 | 5/2007 | Taylor et al. |
| 2007/0251198 A1 | 11/2007 | Witter |
| 2008/0028935 A1 | 2/2008 | Andersson |
| 2008/0116052 A1 | 5/2008 | Eatough et al. |
| 2008/0179165 A1 | 7/2008 | Chen et al. |
| 2008/0250863 A1 | 10/2008 | Moore |
| 2008/0257236 A1 | 10/2008 | Green |
| 2008/0271985 A1 | 11/2008 | Yamasaki |
| 2008/0289305 A1 | 11/2008 | Girondi |
| 2009/0007785 A1 | 1/2009 | Kimura et al. |
| 2009/0032385 A1 | 2/2009 | Engle |
| 2009/0105852 A1 | 4/2009 | Wintrich et al. |
| 2009/0152092 A1 | 6/2009 | Kim et al. |
| 2009/0162269 A1 | 6/2009 | Barger et al. |
| 2009/0217576 A1 | 9/2009 | Kim et al. |
| 2009/0257932 A1 | 10/2009 | Canari et al. |
| 2009/0283395 A1 | 11/2009 | Hippe |
| 2010/0015564 A1 | 1/2010 | Chun et al. |
| 2010/0095521 A1 | 4/2010 | Kartal et al. |
| 2010/0106310 A1 | 4/2010 | Grohman |
| 2010/0113266 A1 | 5/2010 | Abe et al. |
| 2010/0115912 A1 | 5/2010 | Worley |
| 2010/0119425 A1 | 5/2010 | Palmer |
| 2010/0181297 A1 | 7/2010 | Whysail |
| 2010/0196597 A1 | 8/2010 | Di Loreto |
| 2010/0276269 A1 | 11/2010 | Schuecker et al. |
| 2010/0287871 A1 | 11/2010 | Bloom et al. |
| 2010/0300867 A1 | 12/2010 | Kim et al. |
| 2010/0314234 A1 | 12/2010 | Knoch et al. |
| 2011/0000284 A1 | 1/2011 | Kumar et al. |
| 2011/0014406 A1 | 1/2011 | Coleman et al. |
| 2011/0048917 A1 | 3/2011 | Kim et al. |
| 2011/0083314 A1 | 4/2011 | Baird |
| 2011/0088600 A1 | 4/2011 | McRae |
| 2011/0100273 A1 | 5/2011 | Ptacek |
| 2011/0120852 A1 | 5/2011 | Kim |
| 2011/0144406 A1 | 6/2011 | Masatsugu et al. |
| 2011/0156902 A1* | 6/2011 | Wang ............... G05B 23/027 340/540 |
| 2011/0168482 A1 | 7/2011 | Merchant et al. |
| 2011/0174301 A1 | 7/2011 | Haydock et al. |
| 2011/0192395 A1 | 8/2011 | Kim |
| 2011/0198206 A1 | 8/2011 | Kim et al. |
| 2011/0223088 A1 | 9/2011 | Chang et al. |
| 2011/0253521 A1 | 10/2011 | Kim |
| 2011/0291827 A1 | 12/2011 | Baldocchi et al. |
| 2011/0313218 A1 | 12/2011 | Dana |
| 2011/0315538 A1 | 12/2011 | Kim et al. |
| 2012/0031076 A1 | 2/2012 | Frank et al. |
| 2012/0125709 A1 | 5/2012 | Merchant et al. |
| 2012/0152720 A1 | 6/2012 | Reichelt et al. |
| 2012/0177541 A1 | 7/2012 | Mutsuda et al. |
| 2012/0179421 A1 | 7/2012 | Dasgupta |
| 2012/0180133 A1 | 7/2012 | Ai-Harbi et al. |
| 2012/0195815 A1 | 8/2012 | Moore et al. |
| 2012/0228115 A1 | 9/2012 | Westbrook |
| 2012/0247939 A1 | 10/2012 | Kim et al. |
| 2012/0285080 A1 | 11/2012 | Despen et al. |
| 2012/0305380 A1 | 12/2012 | Wang et al. |
| 2012/0312019 A1 | 12/2012 | Rechtman |
| 2013/0020781 A1 | 1/2013 | Kishikawa |
| 2013/0045149 A1 | 2/2013 | Miller |
| 2013/0213114 A1 | 8/2013 | Wetzig et al. |
| 2013/0216717 A1 | 8/2013 | Rago et al. |
| 2013/0220373 A1 | 8/2013 | Kim |
| 2013/0306462 A1 | 11/2013 | Kim et al. |
| 2014/0039833 A1 | 2/2014 | Sharpe, Jr. et al. |
| 2014/0048404 A1* | 2/2014 | Quanci ............... C10B 27/06 201/37 |
| 2014/0156584 A1 | 6/2014 | Motukuri et al. |
| 2014/0208997 A1 | 7/2014 | Alferyev et al. |
| 2014/0224123 A1 | 8/2014 | Walters |
| 2015/0041304 A1 | 2/2015 | Kiim et al. |
| 2015/0075962 A1 | 3/2015 | Shimoyama et al. |
| 2015/0122629 A1 | 5/2015 | Freimuth et al. |
| 2015/0143908 A1 | 5/2015 | Cetinkaya |
| 2015/0175433 A1 | 6/2015 | Micka et al. |
| 2015/0176095 A1 | 6/2015 | Connors et al. |
| 2015/0219530 A1 | 8/2015 | Li et al. |
| 2015/0226499 A1 | 8/2015 | Mikkelsen |
| 2016/0026193 A1 | 1/2016 | Rhodes et al. |
| 2016/0048139 A1 | 2/2016 | Samples et al. |
| 2016/0149944 A1 | 5/2016 | Obermeirer et al. |
| 2016/0154171 A1 | 6/2016 | Kato et al. |
| 2016/0370082 A1 | 12/2016 | Olivo |
| 2016/0377430 A1* | 12/2016 | Kalagnanam ............ G01W 1/10 702/150 |
| 2017/0173519 A1 | 6/2017 | Naito |
| 2017/0182447 A1 | 6/2017 | Sappok et al. |
| 2017/0226425 A1 | 8/2017 | Kim et al. |
| 2017/0261417 A1 | 9/2017 | Zhang |
| 2017/0313943 A1 | 11/2017 | Valdevies |
| 2019/0317167 A1 | 10/2019 | LaBorde et al. |
| 2020/0071190 A1 | 3/2020 | Wiederin et al. |
| 2020/0139273 A1 | 5/2020 | Badiei |
| 2020/0173679 A1 | 6/2020 | O'Reilly et al. |
| 2020/0208059 A1 | 7/2020 | Quanci et al. |
| 2020/0208063 A1 | 7/2020 | Quanci et al. |
| 2021/0130697 A1 | 5/2021 | Quanci et al. |
| 2021/0163823 A1 | 6/2021 | Quanci et al. |
| 2021/0198579 A1 | 7/2021 | Quanci et al. |
| 2021/0261877 A1 | 8/2021 | Despen et al. |
| 2021/0340454 A1 | 11/2021 | Quanci et al. |
| 2021/0363426 A1 | 11/2021 | West et al. |
| 2021/0363427 A1 | 11/2021 | Quanci et al. |
| 2021/0388270 A1 | 12/2021 | Choi et al. |
| 2022/0056342 A1 | 2/2022 | Quanci et al. |
| 2022/0204858 A1 | 6/2022 | West et al. |
| 2022/0204859 A1 | 6/2022 | Crum et al. |
| 2022/0226766 A1 | 7/2022 | Quanci et al. |
| 2022/0251452 A1 | 8/2022 | Quanci et al. |
| 2022/0298423 A1 | 9/2022 | Quanci et al. |
| 2022/0356410 A1 | 11/2022 | Quanci et al. |
| 2023/0012031 A1 | 1/2023 | Quanci et al. |
| 2023/0142380 A1 | 5/2023 | Quanci et al. |
| 2023/0147916 A1 | 5/2023 | Quanci et al. |
| 2023/0258326 A1 | 8/2023 | Quanci et al. |
| 2023/0416629 A1 | 12/2023 | Quanci et al. |
| 2024/0110103 A1 | 4/2024 | Quanci et al. |
| 2024/0229173 A1 | 7/2024 | Quanci et al. |

FOREIGN PATENT DOCUMENTS

| | | |
|---|---|---|
| CA | 2822841 | 7/2012 |
| CA | 2822857 | 7/2012 |
| CA | 2905110 A1 | 9/2014 |
| CN | 87212113 U | 6/1988 |
| CN | 87107195 A | 7/1988 |
| CN | 2064363 U | 10/1990 |
| CN | 2139121 Y | 7/1993 |
| CN | 1092457 A | 9/1994 |
| CN | 1255528 A | 6/2000 |
| CN | 1270983 A | 10/2000 |
| CN | 2528771 Y | 2/2002 |
| CN | 1358822 A | 7/2002 |
| CN | 2521473 Y | 11/2002 |
| CN | 1468364 A | 1/2004 |
| CN | 1527872 A | 9/2004 |
| CN | 2668641 | 1/2005 |
| CN | 1957204 A | 5/2007 |
| CN | 101037603 A | 9/2007 |
| CN | 101058731 A | 10/2007 |
| CN | 101157874 A | 4/2008 |
| CN | 101211495 A | 7/2008 |
| CN | 201121178 Y | 9/2008 |
| CN | 101395248 A | 3/2009 |
| CN | 100510004 C | 7/2009 |
| CN | 101486017 A | 7/2009 |
| CN | 201264981 Y | 7/2009 |
| CN | 101497835 A | 8/2009 |
| CN | 101509427 A | 8/2009 |
| CN | 101886466 A | 11/2010 |
| CN | 101910530 A | 12/2010 |

(56) References Cited

FOREIGN PATENT DOCUMENTS

| | | | |
|---|---|---|---|
| CN | 102072829 A | 5/2011 |
| CN | 102155300 A | 8/2011 |
| CN | 2509188 Y | 11/2011 |
| CN | 202226816 | 5/2012 |
| CN | 202265541 U | 6/2012 |
| CN | 102584294 A | 7/2012 |
| CN | 202415446 U | 9/2012 |
| CN | 202470353 U | 10/2012 |
| CN | 103399536 A | 11/2013 |
| CN | 103468289 A | 12/2013 |
| CN | 103756699 A | 4/2014 |
| CN | 103913193 A | 7/2014 |
| CN | 203981700 U | 12/2014 |
| CN | 104498059 A | 4/2015 |
| CN | 105001914 A | 10/2015 |
| CN | 105137947 A | 12/2015 |
| CN | 105189704 A | 12/2015 |
| CN | 105264448 A | 1/2016 |
| CN | 105467949 A | 4/2016 |
| CN | 106399607 A | 2/2017 |
| CN | 106661456 A | 5/2017 |
| CN | 106687564 A | 5/2017 |
| CN | 107022359 A | 8/2017 |
| CN | 107267183 A | 10/2017 |
| CN | 107445633 A | 12/2017 |
| CN | 100500619 C | 6/2020 |
| CN | 111778048 A | 10/2020 |
| CN | 113322085 A | 8/2021 |
| CN | 113462415 A | 10/2021 |
| CN | 114517099 A | 5/2022 |
| CN | 101921643 B | 12/2022 |
| DE | 201729 C | 9/1908 |
| DE | 212176 | 7/1909 |
| DE | 1212037 B | 3/1966 |
| DE | 2212544 A | 1/1973 |
| DE | 2720688 A1 | 11/1978 |
| DE | 3231697 C1 | 1/1984 |
| DE | 3328702 A1 | 2/1984 |
| DE | 3315738 C2 | 3/1984 |
| DE | 3329367 C | 11/1984 |
| DE | 3407487 C1 | 6/1985 |
| DE | 19545736 | 6/1997 |
| DE | 19803455 | 8/1999 |
| DE | 10122531 A1 | 11/2002 |
| DE | 10154785 | 5/2003 |
| DE | 102004062936 A1 | 7/2006 |
| DE | 102005015301 | 10/2006 |
| DE | 102006004669 | 8/2007 |
| DE | 102006026521 | 12/2007 |
| DE | 102009031436 | 1/2011 |
| DE | 102011052785 | 12/2012 |
| EA | 010510 B1 | 10/2008 |
| EP | 0126399 A1 | 11/1984 |
| EP | 0208490 A1 | 1/1987 |
| EP | 0903393 A2 | 3/1999 |
| EP | 1538503 A1 | 6/2005 |
| EP | 1860034 A1 | 11/2007 |
| EP | 2295129 A1 | 3/2011 |
| EP | 2468837 A1 | 6/2012 |
| FR | 2339664 | 8/1977 |
| FR | 2517802 | 6/1983 |
| FR | 2764978 | 12/1998 |
| GB | 364236 A | 1/1932 |
| GB | 368649 A | 3/1932 |
| GB | 441784 | 1/1936 |
| GB | 606340 | 8/1948 |
| GB | 611524 | 11/1948 |
| GB | 725865 | 3/1955 |
| GB | 783720 A | 9/1957 |
| GB | 871094 | 6/1961 |
| GB | 923205 A | 5/1963 |
| GB | 2000193 A | 1/1979 |
| JP | S50148405 | 11/1975 |
| JP | S5319301 A | 2/1978 |
| JP | 54054101 | 4/1979 |
| JP | S5453103 A | 4/1979 |
| JP | 57051786 | 3/1982 |
| JP | 57051787 | 3/1982 |
| JP | 57083585 | 5/1982 |
| JP | 57090092 | 6/1982 |
| JP | S57172978 A | 10/1982 |
| JP | 58091788 | 5/1983 |
| JP | 59051978 | 3/1984 |
| JP | 59053589 | 3/1984 |
| JP | 59071388 | 4/1984 |
| JP | 59108083 | 6/1984 |
| JP | 59145281 | 8/1984 |
| JP | 60004588 | 1/1985 |
| JP | 61106690 | 5/1986 |
| JP | 62011794 | 1/1987 |
| JP | 62285980 | 12/1987 |
| JP | 01103694 | 4/1989 |
| JP | 01249886 | 10/1989 |
| JP | H0319127 | 3/1991 |
| JP | 03197588 | 8/1991 |
| JP | 04159392 | 6/1992 |
| JP | H04178494 A | 6/1992 |
| JP | H05230466 A | 9/1993 |
| JP | H0649450 A | 2/1994 |
| JP | H0654753 U | 7/1994 |
| JP | H06264062 | 9/1994 |
| JP | H06299156 A | 10/1994 |
| JP | H0776713 A | 3/1995 |
| JP | 07188668 | 7/1995 |
| JP | 07216357 | 8/1995 |
| JP | H07204432 | 8/1995 |
| JP | H0843314 A | 2/1996 |
| JP | H08104875 A | 4/1996 |
| JP | 08127778 | 5/1996 |
| JP | H08218071 A | 8/1996 |
| JP | H09310074 A | 12/1997 |
| JP | H10273672 A | 10/1998 |
| JP | H11131074 | 5/1999 |
| JP | H11256166 A | 9/1999 |
| JP | 2000204373 A | 7/2000 |
| JP | 2000219883 A | 8/2000 |
| JP | 2001055576 A | 2/2001 |
| JP | 2001187887 A | 7/2001 |
| JP | 2001200258 | 7/2001 |
| JP | 2002097472 A | 4/2002 |
| JP | 2002106941 | 4/2002 |
| JP | 2003041258 | 2/2003 |
| JP | 2003051082 A | 2/2003 |
| JP | 2003071313 A | 3/2003 |
| JP | 2003292968 A | 10/2003 |
| JP | 2003342581 A | 12/2003 |
| JP | 2004169016 A | 6/2004 |
| JP | 2005503448 A | 2/2005 |
| JP | 2005135422 A | 5/2005 |
| JP | 2005154597 A | 6/2005 |
| JP | 2005263983 A | 9/2005 |
| JP | 2005344085 A | 12/2005 |
| JP | 2006188608 A | 7/2006 |
| JP | 2007063420 A | 3/2007 |
| JP | 3924064 B2 | 6/2007 |
| JP | 2007169484 A | 7/2007 |
| JP | 2007231326 A | 9/2007 |
| JP | 4101226 B2 | 6/2008 |
| JP | 2008231278 A | 10/2008 |
| JP | 2009019106 A | 1/2009 |
| JP | 2009073864 A | 4/2009 |
| JP | 2009073865 A | 4/2009 |
| JP | 2009135276 A | 6/2009 |
| JP | 2009144121 | 7/2009 |
| JP | 2009209286 A | 9/2009 |
| JP | 2010229239 A | 10/2010 |
| JP | 2010248389 A | 11/2010 |
| JP | 2011504947 A | 2/2011 |
| JP | 2011068733 A | 4/2011 |
| JP | 2011102351 A | 5/2011 |
| JP | 2012072389 A | 4/2012 |
| JP | 2012102302 | 5/2012 |
| JP | 2012102325 A | 5/2012 |
| JP | 2013006957 A | 1/2013 |

(56) References Cited

FOREIGN PATENT DOCUMENTS

| | | |
|---|---|---|
| JP | 2013510910 | 3/2013 |
| JP | 2013189322 A | 9/2013 |
| JP | 2014009284 A | 1/2014 |
| JP | 2014040502 A | 3/2014 |
| JP | 2015094091 A | 5/2015 |
| JP | 2015199791 A | 11/2015 |
| JP | 2016169897 A | 9/2016 |
| JP | 2020007472 A | 1/2020 |
| KR | 1019960008754 | 10/1996 |
| KR | 19990017156 U | 5/1999 |
| KR | 1019990054426 | 7/1999 |
| KR | 20000042375 A | 7/2000 |
| KR | 100296700 B1 | 10/2001 |
| KR | 20030012458 A | 2/2003 |
| KR | 1020040020883 A | 3/2004 |
| KR | 20040107204 A | 12/2004 |
| KR | 20050053861 A | 6/2005 |
| KR | 20060132336 A | 12/2006 |
| KR | 100737393 B1 | 7/2007 |
| KR | 100797852 | 1/2008 |
| KR | 20080069170 A | 7/2008 |
| KR | 20110010452 A | 2/2011 |
| KR | 101314288 | 4/2011 |
| KR | 20120033091 A | 4/2012 |
| KR | 20130050807 | 5/2013 |
| KR | 101318388 | 10/2013 |
| KR | 20140042526 A | 4/2014 |
| KR | 20140076155 A | 6/2014 |
| KR | 20150011084 A | 1/2015 |
| KR | 20150068557 A | 6/2015 |
| KR | 20170038102 A | 4/2017 |
| KR | 20170058808 A | 5/2017 |
| KR | 20170103857 A | 9/2017 |
| KR | 101862491 B1 | 5/2018 |
| RU | 2083532 C1 | 7/1997 |
| RU | 2441898 C2 | 2/2012 |
| RU | 2493233 C2 | 9/2013 |
| SU | 1535880 A1 | 1/1990 |
| TW | 201241166 A1 | 10/2012 |
| TW | 201245431 A1 | 11/2012 |
| UA | 50580 | 10/2002 |
| WO | WO9012074 | 10/1990 |
| WO | WO9945083 | 9/1999 |
| WO | WO02062922 | 8/2002 |
| WO | WO2003025093 | 3/2003 |
| WO | WO2005023649 | 3/2005 |
| WO | WO2005031297 | 4/2005 |
| WO | WO2005115583 | 12/2005 |
| WO | WO2007103649 | 9/2007 |
| WO | WO2008034424 | 3/2008 |
| WO | WO2008105269 | 9/2008 |
| WO | WO2009147983 | 12/2009 |
| WO | WO2010032734 | 3/2010 |
| WO | WO2010103992 | 9/2010 |
| WO | WO2011000447 | 1/2011 |
| WO | WO2011126043 | 10/2011 |
| WO | WO2012029979 | 3/2012 |
| WO | WO2012031726 | 3/2012 |
| WO | WO2013023872 | 2/2013 |
| WO | WO2010107513 | 9/2013 |
| WO | WO2013145679 | 10/2013 |
| WO | WO2013153557 | 10/2013 |
| WO | WO2014021909 | 2/2014 |
| WO | WO2014043667 | 3/2014 |
| WO | WO2014105064 | 7/2014 |
| WO | WO2014153050 | 9/2014 |
| WO | WO2016004106 | 1/2016 |
| WO | WO2016033511 | 3/2016 |
| WO | WO2016033515 | 3/2016 |
| WO | WO2016086322 | 6/2016 |
| WO | WO2016109854 | 7/2016 |
| WO | WO2022159604 | 7/2022 |
| WO | WO2022235839 | 11/2022 |

OTHER PUBLICATIONS

U.S. Appl. No. 17/459,380, filed Jun. 5, 2018, titled Systems and Methods for Removing Mercury From Emissions.
U.S. Appl. No. 17/140,564, filed Jan. 4, 2021, titled Methods and Systems for Improved Coke Quenching.
U.S. Appl. No. 17/155,818, filed Jan. 22, 2021, titled Methods and Systems for Improved Quench Tower Design.
U.S. Appl. No. 17/190,720, filed Mar. 3, 2021, titled Coke Ovens Having Monolith Component Construction.
U.S. Appl. No. 17/172,476, filed Feb. 10, 2021, titled Integrated Coke Plant Automation and Optimization Using Advanced Control and Optimization Techniques.
U.S. Appl. No. 17/521,061, filed Nov. 8, 2021, titled System and Method for Repairing a Coke Oven.
U.S. Appl. No. 16/729,053, filed Dec. 27, 2019, titled Oven Uptakes.
U.S. Appl. No. 17/843,164, filed Jun. 17, 2022, titled Methods and Systems for Providing Corrosion Resistant Surfaces in Contaminant Treatment Systems.
U.S. Appl. No. 17/321,857, filed May 17, 2021, titled Decarbonization of Coke Ovens and Associated Systems and Methods.
U.S. Appl. No. 17/584,672, filed Jan. 26, 2022, titled Heat Recovery Oven Foundation.
U.S. Appl. No. 18/313,647, filed May 8, 2023, titled Spring-Loaded Heat Recovery Oven System and Method.
U.S. Appl. No. 17/306,895, filed May 3, 2021, titled High-Quality Coke Products.
U.S. Appl. No. 18/052,760, filed Nov. 2, 2022, titled Foundry Coke Products, and Associated Systems, Devices, and Methods.
U.S. Appl. No. 18/506,616, filed Nov. 10, 2023, titled Systems and Methods for Removing Mercury From Emissions.
U.S. Appl. No. 18/473,143, filed Sep. 22, 2023, titled Methods and Systems for Improved Coke Quenching.
U.S. Appl. No. 17/471,491, filed Sep. 10, 2021, now U.S. Pat. No. 11,142,699, titled Vent Stack Lids and Associated Systems and Methods.
U.S. Appl. No. 18/363,508, filed Aug. 1, 2023, titled Methods and Systems for Improved Quench Tower Design.
U.S. Appl. No. 18/483,019, filed Oct. 9, 2023, titled Coke Ovens Having Monolith Component Construction.
U.S. Appl. No. 18/473,143, filed Sep. 22, 2023, titled Integrated Coke Plant Automation and Optimization Using Advanced Control and Optimization Techniques.
U.S. Appl. No. 18/469,704, filed Sep. 19, 2023, titled System and Method for Repairing a Coke Oven.
U.S. Appl. No. 18/366,244, filed Aug. 7, 2023, titled Oven Uptakes.
U.S. Appl. No. 18/486,021, filed Oct. 12, 2023, titled Methods and Systems for Providing Corrosion Resistant Surfaces in Contaminant Treatment Systems.
U.S. Appl. No. 17/306,895, now U.S. Pat. No. 11,767,482, filed May 3, 2021, now U.S. Pat. No. 11,767,482, titled High-Quality Coke Products.
U.S. Appl. No. 18/052,739, filed Nov. 4, 2022, titled Foundry Coke Products and Associated Processing Methods Via Cupolas.
U.S. Appl. No. 07/587,742, filed Sep. 25, 1990, now U.S. Pat. No. 5,114,542, titled Nonrecovery Coke Oven Battery and Method of Operation.
U.S. Appl. No. 07/878,904, filed May 6, 1992, now U.S. Pat. No. 5,318,671, titled Method of Operation of Nonrecovery Coke Oven Battery.
U.S. Appl. No. 09/783,195, filed Feb. 14, 2001, now U.S. Pat. No. 6,596,128, titled Coke Oven Flue Gas Sharing.
U.S. Appl. No. 07/886,804, filed May 22, 1992, now U.S. Pat. No. 5,228,955, titled High Strength Coke Oven Wall Having Gas Flues Therein.
U.S. Appl. No. 08/059,673, filed May 12, 1993, now U.S. Pat. No. 5,447,606, titled Method of and Apparatus for Capturing Coke Oven Charging Emissions.
U.S. Appl. No. 08/914,140, filed Aug. 19, 1997, now U.S. Pat. No. 5,928,476, titled Nonrecovery Coke Oven Door.
U.S. Appl. No. 09/680,187, filed Oct. 5, 2000, now U.S. Pat. No. 6,290,494, titled Method and Apparatus for Coal Coking.

(56) References Cited

OTHER PUBLICATIONS

U.S. Appl. No. 10/933,866, filed Sep. 3, 2004, now U.S. Pat. No. 7,331,298, titled Coke Oven Rotary Wedge Door Latch.
U.S. Appl. No. 11/424,566, filed Jun. 16, 2006, now U.S. Pat. No. 7,497,930, titled Method and Apparatus for Compacting Coal for a Coal Coking Process.
U.S. Appl. No. 12/405,269, filed Mar. 17, 2009, now U.S. Pat. No. 7,998,316, titled Flat Push Coke Wet Quenching Apparatus and Process.
U.S. Appl. No. 13/205,960, filed Aug. 9, 2011, now U.S. Pat. No. 9,321,965, titled Flat Push Coke Wet Quenching Apparatus and Process.
U.S. Appl. No. 11/367,236, filed Mar. 3, 2006, now U.S. Pat. No. 8,152,970, titled Method and Apparatus for Producing Coke.
U.S. Appl. No. 12/403,391, filed Mar. 13, 2009, now U.S. Pat. No. 8,172,930, titled Cleanable in Situ Spark Arrestor.
U.S. Appl. No. 12/849,192, filed Aug. 3, 2010, now U.S. Pat. No. 9,200,225, titled Method and Apparatus for Compacting Coal for a Coal Coking Process.
U.S. Appl. No. 13/631,215, filed Sep. 28, 2012, now U.S. Pat. No. 9,683,740, titled Methods for Handling Coal Processing Emissions and Associated Systems and Devices.
U.S. Appl. No. 13/730,692, filed Dec. 28, 2012, now U.S. Pat. No. 9,193,913, titled Reduced Output Rate Coke Oven Operation With Gas Sharing Providing Extended Process Cycle.
U.S. Appl. No. 14/655,204, now U.S. Pat. No. 10,016,714, filed Jun. 24, 2015, titled Systems and Methods for Removing Mercury From Emissions.
U.S. Appl. No. 16/000,516, now U.S. Pat. No. 11,117,087, filed Jun. 5, 2018, titled Systems and Methods for Removing Mercury From Emissions.
U.S. Appl. No. 17/459,380, now, U.S. Pat. No. 11,845,037, filed Jun. 5, 2018, titled Systems and Methods for Removing Mercury From Emissions.
U.S. Appl. No. 13/830,971, filed Mar. 14, 2013, now U.S. Pat. No. 10,047,296, titled Non-Perpendicular Connections Between Coke Oven Uptakes and a Hot Common Tunnel, and Associated Systems and Methods, now U.S. Pat. No. 10,047,295.
U.S. Appl. No. 16/026,363, filed Jul. 3, 2018, now U.S. Pat. No. 11,008,517, titled Non-Perpendicular Connections Between Coke Oven Uptakes and a Hot Common Tunnel, and Associated Systems and Methods.
U.S. Appl. No. 13/730,796, filed Dec. 28, 2012, now U.S. Pat. No. 10,883,051, titled Methods and Systems for Improved Coke Quenching.
U.S. Appl. No. 17/140,564, filed Jan. 4, 2021, now U.S. Pat. No. 11,807,812, titled Methods and Systems for Improved Coke Quenching.
U.S. Appl. No. 13/730,598, filed Dec. 28, 2012, now U.S. Pat. No. 9,238,778, titled Systems and Methods for Improving Quenched Coke Recovery.
U.S. Appl. No. 14/952,267, filed Nov. 25, 2015, now U.S. Pat. No. 9,862,888, titled Systems and Methods for Improving Quenched Coke Recovery.
U.S. Appl. No. 15/830,320, filed Dec. 4, 2017, now U.S. Pat. No. 10,323,192, titled Systems and Methods for Improving Quenched Coke Recovery.
U.S. Appl. No. 13/730,735, filed Dec. 28, 2012, now U.S. Pat. No, 9,273,249, titled Systems and Methods for Controlling Air Distribution in a Coke Oven.
U.S. Appl. No. 14/655,013, filed Jun. 23, 2015, now U.S. Pat. No. 11,142,699, titled Vent Stack Lids and Associated Systems and Methods.
U.S. Appl. No. 17/471,491, filed Sep. 10, 2021, now U.S. Pat. No. 11,939,526, titled Vent Stack Lids and Associated Systems and Methods.
U.S. Appl. No. 13/843,166, filed Mar. 15, 2013, now U.S. Pat. No. 9,273,250, titled Methods and Systems for Improved Quench Tower Design.
U.S. Appl. No. 15/014,547, filed Feb. 3, 2016, now, U.S. Pat. No. 10,927,303, titled Methods for Improved Quench Tower Design.
U.S. Appl. No. 17/155,818, filed Jan. 22, 2021, now U.S. Pat. No. 11,746,296, titled Methods and Systems for Improved Quench Tower Design.
U.S. Appl. No. 14/655,003, filed Jun. 23, 2015, now U.S. Pat. No. 10,760,002, titled Systems and Methods for Maintaining a Hot Car in a Coke Plant.
U.S. Appl. No. 16/897,957, filed Jun. 10, 2020, now U.S. Pat. No. 11,359,145, titled Systems and Methods for Maintaining a Hot Car in a Coke Plant.
U.S. Appl. No. 13/829,588, filed Mar. 14, 2013, now U.S. Pat. No. 9,193,915, titled Horizontal Heat Recovery Coke Ovens Having Monolith Crowns.
U.S. Appl. No. 15/322,176, filed Dec. 27, 2016, now U.S. Pat. No. 10,526,541, titled Horizontal Heat Recovery Coke Ovens Having Monolith Crowns.
U.S. Appl. No. 15/511,036, filed Mar. 14, 2017, now U.S. Pat. No. 10,968,383, titled Coke Ovens Having Monolith Component Construction.
U.S. Appl. No. 17/190,720, now U.S. Pat. No. 11,795,400, filed Mar. 3, 2021, titled Coke Ovens Having Monolith Component Construction.
U.S. Appl. No. 13/589,009, filed Aug. 17, 2012, now U.S. Pat. No. 9,359,554, titled Automatic Draft Control System for Coke Plants.
U.S. Appl. No. 15/139,568, filed Apr. 27, 2016, now U.S. Pat. No. 10,947,455, titled Automatic Draft Control System for Coke Plants.
U.S. Appl. No. 17/176,391, now U.S. Pat. No. 11,692,138, filed Feb. 16, 2021, titled Automatic Draft Control System for Coke Plants.
U.S. Appl. No. 18/321,530, filed May 22, 2023, titled Automatic Draft Control System for Coke Plants.
U.S. Appl. No. 13/588,996, filed Aug. 17, 2012, now U.S. Pat. No. 9,243,186, titled Coke Plant Including Exhaust Gas Sharing.
U.S. Appl. No. 14/959,450, filed Dec. 4, 2015, now U.S. Pat. No. 10,041,002, titled Coke Plant Including Exhaust Gas Sharing.
U.S. Appl. No. 16/047,198, filed Jul. 27, 2018, now U.S. Pat. No. 10,611,965, titled Coke Plant Including Exhaust Gas Sharing.
U.S. Appl. No. 16/828,448, filed Mar. 24, 2020, now U.S. Pat. No. 11,441,077, titled Coke Plant Including Exhaust Gas Sharing.
U.S. Appl. No. 13/589,004, filed Aug. 17, 2012, now U.S. Pat. No. 9,249,357, titled Method and Apparatus for Volatile Matter Sharing in Stamp-Charged Coke Ovens.
U.S. Appl. No. 13/730,673, filed Dec. 28, 2012, now U.S. Pat. No. 9,476,547, titled Exhaust Flow Modifier, Duct Intersection Incorporating the Same, and Methods Therefor.
U.S. Appl. No. 15/281,891, filed Sep. 30, 2016, now U.S. Pat. No. 10,975,309, titled Exhaust Flow Modifier, Duck Intersection Incorporating the Same, and Methods Therefor.
U.S. Appl. No. 17/191,119, filed Mar. 3, 3021, titled Exhaust Flow Modifier, Duck Intersection Incorporating the Same, and Methods Therefor.
U.S. Appl. No. 13/598,394, filed Aug. 29, 2012, now U.S. Pat. No. 9,169,439, titled Method and Apparatus for Testing Coal Coking Properties.
U.S. Appl. No. 14/865,581, filed Sep. 25, 2015, now U.S. Pat. No. 10,053,627, titled Method and Apparatus for Testing Coal Coking Properties, now U.S. Pat. No. 10,053,627.
U.S. Appl. No. 14/839,384, filed Aug. 28, 2015, now U.S. Pat. No. 9,580,656, titled Coke Oven Charging System.
U.S. Appl. No. 15/443,246, filed Feb. 27, 2017, now U.S. Pat. No. 9,976,089, titled Coke Oven Charging System.
U.S. Appl. No. 14/587,670, filed Dec. 31, 2014, now U.S. Pat. No. 10,619,101, titled Methods for Decarbonizing Coking Ovens, and Associated Systems and Devices.
U.S. Appl. No. 16/845,530, filed Apr. 10, 2020, now U.S. Pat. No. 11,359,146, titled Methods for Decarbonizing Coking Ovens, and Associated Systems and Devices.
U.S. Appl. No. 14/984,489, filed Dec. 30, 2015, now U.S. Pat. No. 10,975,310, titled Multi-Modal Beds of Coking Material.
U.S. Appl. No. 14/983,837, filed Dec. 30, 2015, now U.S. Pat. No. 10,968,395, titled Multi-Modal Beds of Coking Material.
U.S. Appl. No. 14/986,281, filed Dec. 31, 2015, now U.S. Pat. No. 10,975,311, titled Multi-Modal Beds of Coking Material.

(56) References Cited

OTHER PUBLICATIONS

U.S. Appl. No. 17/222,886, filed Apr. 12, 2021, titled Multi-Modal Beds of Coking Material.
U.S. Appl. No. 14/987,625, filed Jan. 4, 2016, now U.S. Pat. No. 11,060,032, titled Integrated Coke Plant Automation and Optimization Using Advanced Control and Optimization Techniques.
U.S. Appl. No. 17/172,476, filed Feb. 10, 2021, now U.S. Pat. No. 11,788,012, titled Integrated Coke Plant Automation and Optimization Using Advanced Control and Optimization Techniques.
U.S. Appl. No. 14/839,493, filed Aug. 28, 2015, now U.S. Pat. No. 10,233,392, titled Method and System for Optimizing Coke Plant Operation and Output.
U.S. Appl. No. 16/251,352, filed Jan. 18, 2019, now U.S. Pat. No. 11,053,444, titled Method and System for Optimizing Coke Plant Operation and Output.
U.S. Appl. No. 14/839,551, filed Aug. 28, 2015, now U.S. Pat. No. 10,308,876, titled Burn Profiles for Coke Operations.
U.S. Appl. No. 16/428,014, filed May 31, 2019, now U.S. Pat. No. 10,920,148, titled Improved Burn Profiles for Coke Operations.
U.S. Appl. No. 17/155,719, filed Jan. 22, 2021, now U.S. Pat. No. 11,441,078, titled Improved Burn Profiles for Coke Operations.
U.S. Appl. No. 14/839,588, filed Aug. 28, 2015, now U.S. Pat. No. 9,708,542, titled Method and System for Optimizing Coke Plant Operation and Output.
U.S. Appl. No. 15/392,942, filed Dec. 28, 2016, now U.S. Pat. No. 10,526,542, titled Method and System for Dynamically Charging a Coke Oven.
U.S. Appl. No. 16/735,103, filed Jan. 6, 2020, now U.S. Pat. No. 11,214,739, titled Method and System for Dynamically Charging a Coke Oven.
U.S. Appl. No. 15/614,525, filed Jun. 5, 2017, now U.S. Pat. No. 11,508,230, titled Methods and Systems for Automatically Generating a Remedial Action in an Industrial Facility.
U.S. Appl. No. 15/987,860, filed May 23, 2018, now U.S. Pat. No. 10,851,306, titled System and Method for Repairing a Coke Oven.
U.S. Appl. No. 17/076,563, filed Oct. 21, 2020, now U.S. Pat. No. 11,186,778, titled System and Method for Repairing a Coke Oven.
U.S. Appl. No. 17/521,061, now U.S. Pat. No. 11,845,898, filed Nov. 8, 2021, titled System and Method for Repairing a Coke Oven.
U.S. Appl. No. 17/135,483, filed Dec. 28, 2020, titled Oven Health Optimization Systems and Methods.
U.S. Appl. No. 16/729,053, filed Dec. 27, 2019, now U.S. Pat. No. 11,760,937, titled Oven Uptakes.
U.S. Appl. No. 16/729,036, filed Dec. 27, 2019, now U.S. Pat. No. 11,365,355, titled Systems and Methods for Treating a Surface of a Coke Plant.
U.S. Appl. No. 17/747,708, filed May 18, 2022, titled Systems and Methods for Treating a Surface of a Coke Plant.
U.S. Appl. No. 18/770,264, filed Jul. 11, 2024, titled Systems and Methods for Treating a Surface of a Coke Plant.
U.S. Appl. No. 16/729,201, filed Dec. 27, 2019, titled Gaseous Tracer Leak Detection.
U.S. Appl. No. 16/729,122, filed Dec. 27, 2019, now U.S. Pat. No. 11,395,989, titled Methods and Systems for Providing Corrosion Resistant Surfaces in Contaminant Treatment Systems.
U.S. Appl. No. 17/843,164, filed Jun. 17, 2022, now U.S. Pat. No. 11,819,802, titled Methods and Systems for Providing Corrosion Resistant Surfaces in Contaminant Treatment Systems.
U.S. Appl. No. 16/729,068, filed Dec. 27, 2019, now U.S. Pat. No. 11,486,572, titled Systems and Methods for Utilizing Flue Gas.
U.S. Appl. No. 17/947,520, filed Sep. 19, 2022, titled Systems and Methods for Utilizing Flue Gas.
U.S. Appl. No. 16/729,129, filed Dec. 27, 2019, now U.S. Pat. No. 11,008,518, titled Coke Plant Tunnel Repair and Flexible Joints.
U.S. Appl. No. 17/320,343, filed May 14, 2021, now U.S. Pat. No. 11,597,881, titled Coke Plant Tunnel Repair and Flexible Joints.
U.S. Appl. No. 18/168,142, filed Feb. 13, 2023, titled Coke Plant Tunnel Repair and Flexible Joints.
U.S. Appl. No. 16/729,170, now U.S. Pat. No. 11,193,069, filed Dec. 27, 2019, titled Coke Plant Tunnel Repair and Anchor Distribution.
U.S. Appl. No. 17/532,058, now U.S. Pat. No. 11,505,747, filed Nov. 22, 2021, titled Coke Plant Tunnel Repair and Anchor Distribution.
U.S. Appl. No. 17/967,615, filed Oct. 17, 2022, titled Coke Plant Tunnel Repair and Anchor Distribution.
U.S. Appl. No. 16/729,157, filed Dec. 27, 2019, now U.S. Pat. No. 11,071,935, titled Particulate Detection for Industrial Facilities, and Associated Systems and Methods.
U.S. Appl. No. 16/729,057, filed Dec. 27, 2019, now U.S. Pat. No. 11,021,655, titled Decarbonization of Coke Ovens and Associated Systems and Methods.
U.S. Appl. No. 17/321,857, filed May 17, 2021, now U.S. Pat. No. 11,643,602, titled Decarbonization of Coke Ovens and Associated Systems and Methods.
U.S. Appl. No. 18/313,622, filed May 8, 2023, titled Decarbonization of Coke Ovens and Associated Systems and Methods.
U.S. Appl. No. 16/729,212, filed Dec. 27, 2019, now U.S. Pat. No. 11,261,381, titled Heat Recovery Oven Foundation.
U.S. Appl. No. 17/584,672, now U.S. Pat. No. 11,845,897, filed Jan. 26, 2022, titled Heat Recovery Oven Foundation.
U.S. Appl. No. 18/492,913, filed Oct. 24, 2023, titled Heat Recovery Oven Foundation.
U.S. Appl. No. 16/729,219, now U.S. Pat. No. 11,098,252, filed Dec. 27, 2019, titled Spring-Loaded Heat Recovery Oven System and Method.
U.S. Appl. No. 17/388,874, filed Jul. 29, 2021, now, U.S. Pat. No. 11,680,208, titled Spring-Loaded Heat Recovery Oven System and Method.
U.S. Appl. No. 17/736,960, filed May 20, 2022, titled Foundry Coke Products, and Associated Systems and Methods.
U.S. Appl. No. 17/306,895, now U.S. Pat. No. 11,767,482, filed on May 3, 2021, now U.S. Pat. No. 11,767,482, titled High-Quality Coke Products.
U.S. Appl. No. 18/363,465, filed Aug. 1, 2023, titled High-Quality Coke Products.
U.S. Appl. No. 18/466,549, filed Sep. 13, 2023, titled High-Quality Coke Products.
U.S. Appl. No. 18/793,631, filed Aug. 2, 2024, titled High-Quality Coke Products.
U.S. Appl. No. 18/501,488, filed Nov. 3, 2023, titled Coal Blends, Foundry Coke Products, and Associated Systems, Devices, and Methods.
U.S. Appl. No. 18/501,795, filed Nov. 3, 2023, titled Coal Blends, Foundry Coke Products, and Associated Systems, Devices, and Methods.
U.S. Appl. No. 18/052,739, filed Nov. 4, 2022, now U.S. Pat. No. 11,946,108, titled Foundry Coke Products and Associated Processing Methods Via Cupolas.
U.S. Appl. No. 18/586,236, filed Feb. 23, 2024, titled Foundry Coke Products and Associated Processing Methods Via Cupolas.
U.S. Appl. No. 18/052,760, filed Nov. 2, 2022, now U.S. Pat. No. 11,851,724, titled Foundry Coke Products, and Associated Systems, Devices, and Methods.
U.S. Appl. No. 18/506,746, filed Nov. 10, 2023, titled Foundry Coke Products, and Associated Systems, Devices, and Methods.
U.S. Appl. No. 18/511,148, filed Nov. 16, 2023, titled Products Comprising Char and Carbon, and Associated Systems, Devices, and Methods.
U.S. Appl. No. 18/511,621, filed Nov. 16, 2023, titled Pelletized Products and Associated Systems, Devices, and Methods.
U.S. Appl. No. 18/770,274, filed Jul. 11, 2024, Quanci et al.
U.S. Appl. No. 18/793,631, filed Aug. 2, 2024, Quanci et al.
Item HT 56107 Briquette, 'H' Type Household or Domestic Use, SECV Brown Coal Mine, Yallourn, Victoria, circa 1925, Museums Victoria Collections, https://collections.museumsvictoria.com.au/items/2286568, published on Mar. 2, 2021; 3 pages.
Office of the Federal Register, National Archives and Records Administration. (Apr. 14, 2005). 70 FR 19992—National Emission Standards for Coke Oven Batteries. [Government]. Office of the

(56) References Cited

OTHER PUBLICATIONS

Federal Register, National Archives and Records Administration. https://www.govinfo.gov/app/details/FR-2005-04-15/05-6942.
Examination Report for European Application No. 17807675.8; Date of Mailing: Jun. 24, 2024; 4 pages.
U.S. Appl. No. 18/313,622, filed May 8, 2023, Quanci et al.
U.S. Appl. No. 18/466,549, filed Sep. 13, 2023, Quanci et al.
U.S. Appl. No. 18/469,704, filed Sep. 19, 2023, Crum et al.
U.S. Appl. No. 18/473,135, filed Sep. 22, 2023, Quanci et al.
U.S. Appl. No. 18/473,143, filed Sep. 22, 2023, Quanci et al.
U.S. Appl. No. 18/483,019, filed Oct. 9, 2023, West et al.
U.S. Appl. No. 18/486,021, filed Oct. 12, 2023, Quanci et al.
U.S. Appl. No. 18/492,913, filed Oct. 24, 2023, Quanci et al.
U.S. Appl. No. 18/501,488, filed Nov. 3, 2023, Quanci et al.
U.S. Appl. No. 18/501,795, filed Nov. 3, 2023, Quanci et al.
U.S. Appl. No. 18/506,616, filed Nov. 10, 2023, Quanci et al.
U.S. Appl. No. 18/506,746, filed Nov. 10, 2023, Quanci et al.
U.S. Appl. No. 18/511,148, filed Nov. 16, 2023, Quanci et al.
U.S. Appl. No. 18/511,621, filed Nov. 16, 2023, Quanci et al.
Chaudhari, K., Cupola Furnace, engineersgalary.com Jan. 24, 2016; 4 pages.
Ishiwata, et al. "Effect of coke diameter and oxygen concentration of blast on cupola operation." ISIJ International, 2011, vol. 51, pp. 1353-1359.
Ivanova, V. A. "Analysis of the requirements for foundry coke." IOP Conference Series: Materials Science and Engineering, 2020, vol. 986, pp. 1-6.
Pearson, D.E., "Influence of Geology on CSR (Coke Strength After Reaction with C02)," 2009, 8 pages.
Powell, et al. "Cupola Furnaces", ASM International, downloaded from http://dl.asminternational.org/handbooks/edited-volume/chapter-pdf/501030/a0005197.pdf; 9 pages.
Examination Report of Brazilian Application No. BR112018074924-9; Date of Mailing: Dec. 5, 2023; 19 pages.
Vietnam Office Action for Vietnam Application No. 1-2018-05261; Date of Mailing: Aug. 29, 2023; 4 pages.
U.S. Appl. No. 17/947,520, filed Sep. 19, 2022, Quanci et al.
U.S. Appl. No. 17/967,615, filed Oct. 17, 2022, Quanci et al.
U.S. Appl. No. 18/168,142, filed Feb. 13, 2023, Quanci et al.
U.S. Appl. No. 18/313,647, filed May 8, 2023, Quanci et al.
U.S. Appl. No. 18/321,530, filed May 22, 2023, Quanci et al.
U.S. Appl. No. 18/363,465, filed Aug. 1, 2023, Quanci et al.
U.S. Appl. No. 18/363,508, filed Aug. 1, 2023, Choi et al.
U.S. Appl. No. 18/366,244, filed Aug. 7, 2023, Quanci et al.
"ASBESTOS", Virginia Department of Health, https://www.vdh.virginia.gov/environmental-health/public-health-toxicology/asbestos/, updated 2023, 2 pages.
ASTM D5341-99(2010)e1, Standard Test Method for Measuring Coke Reactivity Index (CRI) and Coke Strength After Reaction (CSR), ASTM International, West Conshohocken, PA, 2010.
Astrom, et al., "Feedback Systems: An Introduction for Scientists and Engineers," Sep. 16, 2006, available on line at http://people/duke.edu/-hpgavin/SystemID/References/Astrom-Feedback-2006.pdf ; 404 pages.
Basset et al., "Calculation of steady flow pressure loss coefficients for pipe junctions," Proc Instn Mech Engrs., vol. 215, Part C, p. 861-881 IMechIE 2001.
Beckman et al., "Possibilities and limits of cutting back coking plant output," Stahl Und Eisen, Verlag Stahleisen, Dusseldorf, DE, vol. 130, No. 8, Aug. 16, 2010, pp. 57-67.
Bloom, et al., "Modular cast block—The future of coke oven repairs," Iron & Steel Technol, AIST, Warrendale, PA, vol. 4, No. 3, Mar. 1, 2007, pp. 61-64.
Boyes, Walt. (2003), Instrumentation Reference Book (3rd Edition)—34.7.4.6 Infrared and Thermal Cameras, Elsevier. Online version available at: https://app.knovel.com/hotlink/pdf/id:kt004QMGV6/instrumentation-reference-2/ditigal-video.
"Ceramic fibers wool—to 1,300°C", gTeek, Dec. 29, 2017 (date obtained from google search tools), https://www.gteek.com/ceramic-fibers-wool-to1-300-%C2%BOC, 15 pages.
Clean coke process: process development studies by USS Engineers and Consultants, Inc., Wisconsin Tech Search, request date Oct. 5, 2011, 17 pages.
"Conveyor Chain Designer Guild", Mar. 27, 2014 (date obtained from wayback machine), Renold.com, Section 4, available online at: http://www.renold/com/upload/renoldswitzerland/conveyor_chain_-_designer_guide.pdf.
Costa, et al., "Edge Effects on the Flow Characteristics in a 90 deg Tee Junction," Transactions of the ASME, Nov. 2006, vol. 128, pp. 1204-1217.
Crelling, et al., "Effects of Weathered Coal on Coking Properties and Coke Quality", Fuel, 1979, vol. 58, Issue 7, pp. 542-546.
Database WPI, Week 199115, Thomson Scientific, Lond, GB; AN 1991-107552.
De Cordova, et al. "Coke oven life prolongation—A multidisciplinary approach." 10.5151/2594-357X-2610 (2015) 12 pages.
Diez, et al., "Coal for Metallurgical Coke Production: Predictions of Coke Quality and Future Requirements for Cokemaking", International Journal of Coal Geology, 2002, vol. 50, Issue 1-4, pp. 389-412.
"High Alumina Cement-Manufacture, Characteristics and Uses," TheConstructor.org, https://theconstructor.org/concrete/high-alumina-cement/23686/; 12 pages.
"How Glass Is Made," Corning, https://www.corning.com/worldwide/en/innovation/materials-science/glass/how-glass-made.html, 2 pages.
Industrial Furnace Design Handbook, Editor-in-Chief: First Design Institute of First Ministry of Machinery Industry, Beijing: Mechanical Industry Press, pp. 180-183, Oct. 1981.
Joseph, B., "A tutorial on inferential control and its applications," Proceedings of the 1999 American Control Conference (Cat. No. 99CH36251), San Diego, CA, 1999, pp. 3106-3118 vol. 5.
Kerlin, Thomas (1999), Practical Thermocouple Thermometry-1.1 The Thermocouple. ISA. Online version available at https:app.knovel.com/pdf/id:kt007XPTM3/practical-thermocouple/the-thermocouple.
Kochanski et al., "Overview of Uhde Heat Recovery Cokemaking Technology," AISTech Iron and Steel Technology Conference Proceedings, Association for Iron and Steel Technology, U.S., vol. 1, Jan. 1, 2005, pp. 25-32.
Knoerzer et al. "Jewell-Thompson Non-Recovery Cokemaking", Steel Times, Fuel & Metallurgical Journals Ltd. London, GB, vol. 221, No. 4, Apr. 1, 1993, pp. 172-173,184.
Kusiorowski, et al., "Thermal decomposition of different types of absestos, "Journal of Thermal Analysis and Calorimetry . Feb. 2012, 109, 693-704 (2012).
Lin, Rongying et al., "Study on the synergistic effect of calcium and aluminum on improving ash fusion temperature of semi-coke," International Journal of Coal Preparation and Utilization, May 31, 2019 (published online), vol. 42, No. 3, pp. 556-564.
Lipunov, et al. "Diagnostics of the Heating System and Lining of Coke Ovens," Coke and Chemistry, 2014, Vopl. 57, No. 12, pp. 489-492.
Madias, et al., "A review on stamped charging of coals" (2013). Available at https://www.researchgate.net/publication/263887759_A_review_on_stamped_charging_of_coals.
Metallurgical Coke MSDS, ArcelorMittal, May 30, 2011, available online at http://dofasco.arcelormittal.com/-/media/Files/A/Arcelormittal-Canada/material-safety/metallurgical-coke.pdf.
"Middletown Coke Company HRSG Maintenance BACT Analysis Option 1—Individual Spray Quenches Sun Heat Recovery Coke Facility Process Flow Diagram Middletown Coke Company 100 Oven Case #1 -24.5 VM", (Sep. 1, 2009), URL: http://web.archive.org/web/20090901042738/http://epa.ohio.gov/portals/27/transfer/ptiApplication/mcc/new/262504.pdf, (Feb. 12, 2016), XP055249803 [X] 1-13 * p. 7 * * pp. 8-11 *.
Practical Technical Manual of Refractories, Baoyu Hu, etc., Beijing: Metallurgical Industry Press, Chapter 6; 2004, 6-30.
Refractories for Ironmaking and Steelmaking: A History of Battles over High Temperatures; Kyoshi Sugita (Japan, Shaolin Zhang), 1995, p. 160, 2004, 2-29.
"Refractory Castables," Victas.com, Dec. 28, 2011 (date obtained from WayBack Machine), https://www/vitcas.com/refractory-castables; 5 pages.

(56) References Cited

OTHER PUBLICATIONS

Rose, Harold J., "The Selection of Coals for the Manufacture of Coke," American Institute of Mining and Metallurgical Engineers, Feb. 1926, 8 pages.
Tiwari, et al., "A novel technique for assessing the coking potential of coals/cole blends for non-recovery coke making process," Fuel, vol. 107, May 2013, pp. 615-622.
Waddell, et al., "Heat-Recovery Cokemaking Presentation," Jan. 1999, pp. 1-25.
Walker D N et al, "Sun Coke Company's heat recovery cokemaking technology high coke quality and low environmental impact", Revue De Metallurgie—Cahiers D'informations Techniques, Revue De Metallurgie. Paris, FR, (Mar. 1, 2003), vol. 100, No. 3, ISSN 0035-1563, p. 23.
Westbrook, "Heat-Recovery Cokemaking at Sun Coke," AISE Steel Technology, Pittsburg, PA, vol. 76, No. 1, Jan. 1999, pp. 25-28.
"What is dead-band control," forum post by user "wireaddict" on AllAboutCircuits.com message board, Feb. 8, 2007, accessed Oct. 24, 2018 at https:/forum.allaboutcircuits.com/threads/what-is-dead-band-control.4728/; 8 pages.
Yu et al., "Coke Oven Production Technology," Lianoning Science and Technology Press, first edition, Apr. 2014, pp. 356-358.
"Resources and Utilization of Coking Coal in China," Mingxin Shen ed., Chemical Industry Press, first edition, Jan. 2007, pp. 242-243, 247.
Australian Examination Report No. 1 for Australian Application No. 2017272377; Date of Mailing: Mar. 30, 2021; 4 pages.
Brazilian Office Action in Brazilian Application No. BR112018074924-9; Date of Mailing: May 23, 2023; 8 pages.
Canadian Office Action in Canadian Application No. 3,206,379; Date of Mailing: Jul. 14, 2023; 3 pages.
Chinese Office Action in Chinese Application No. 201780036280.3; Date of Mailing: May 31, 2021; 21 pages.
Chinese Office Action in Chinese Application No. 201780036280.3; Date of Mailing: Mar. 18, 2022; 19 pages.
Colombian Office Action for Colombian Application No. NC2018/0012521; Date of Mailing: Jul. 8, 2021; 13 pages.
Extended European Search Report for European Application No. 17807675.8; Date of Mailing: Dec. 16, 2019; 9 pages.
Examination Report for European Application No. 17807675.8; Date of Mailing: Dec. 15, 2021; 5 pages.
International Search Report and Written Opinion for PCT/US2017/036013; Date of Mailing: Sep. 15, 2017; 16 pages.
Japanese Notice of Rejection for Japanese Application No. 2018-563170; Date of Mailing: Mar. 2, 2021; 8 pages.
Japanese Notice of Rejection for Japanese Application No. 2018-563170; Date of Mailing: Oct. 26, 2021; 5 pages.
Korean Office Action for Korean Application No. 10-2018-7036900; Date of Mailing: Aug. 30, 2021; 19 pages.
Mexican Office Action in Mexican Application No. MX/a/2018/000954; Date of Mailing: May 10, 2021; 5 pages.
Russian Office Action for Russian Application No. 2018142296/11 (070508); Date of Mailing: Sep. 30, 2020; 14 pages.
Ukraine Office Action for Ukraine Application No. a 2018 11733; Date of Mailing: Apr. 19, 2022; 5 pages.

\* cited by examiner

METHODS AND SYSTEMS FOR AUTOMATICALLY GENERATING A REMEDIAL ACTION IN AN INDUSTRIAL FACILITY

CROSS-REFERENCE TO RELATED APPLICATION(S)

This application is a continuation of U.S. patent application Ser. No. 15/614,525, filed Jun. 5, 2017, which claims the benefit of priority to U.S. Provisional Patent Application No. 62/345,717, filed Jun. 3, 2016, the disclosures of which are incorporated herein by reference in their entireties.

TECHNICAL FIELD

The present technology is generally directed to using sensors to predict a likelihood of an undesirable event occurrence and automatically generate a remedial action.

BACKGROUND

Coke is a solid carbon fuel and carbon source used to melt and reduce iron ore in the production of steel. In one process, known as the "Thompson Coking Process," coke is produced by batch feeding pulverized coal to an oven that is sealed and heated to very high temperatures for approximately forty-eight hours under closely-controlled atmospheric conditions. Coking ovens have been used for many years to convert coal into metallurgical coke. During the coking process, finely crushed coal is heated under controlled temperature conditions to devolatilize the coal and form a fused mass of coke having a predetermined porosity and strength. The hot coke is then pushed from the oven into hot cars that transport the coke to quench towers to be cooled. The quenched coke is discharged onto an inclined coke wharf where it is crushed, screened and transported off-site as product. Throughout the coke-producing process, emissions of various materials are commonly produced. For example, steam is generated during the quenching process and particulate matter is generated during the coke pushing process.

Coking facilities are commonly located in industrial areas near other industrial facilities, including those that produce steel, industrial gases, steam, and various chemicals. Given the industrial nature of the neighboring industrial facilities, emissions from these industrial facilities can disperse and migrate to the other industrial facilities located nearby. For example, many of the industrial facilities combust natural gas to form flue gas that is used to heat different process streams. The sulfur present in natural gas can remain in the flue gas and is often released via flue gas stacks. Sulfur can also be released during other processing stages such as, for example, quenching or wharf operations. The sulfur, in its various forms, emitted from one industrial facility can disperse toward another industrial facility and eventually to the surrounding public community. The dispersion, which may have unpleasant odor characteristics, is perceived by individuals of the public community and can result in complaints being directed to local regulatory agencies. Naturally, the individuals reporting the complaint are unaware of the source of the dispersion and thus the complaints are often directed toward the company or facility that the individual is most aware of. To prevent any such complaints from occurring, there exists a need to better predict a likelihood of the occurrence of undesirable events to enable facilities to prevent the actual occurrence of the events or mitigate effects of the occurrence of the events. Additionally, there is a need to identify the emissions source and proactively notify the public that the emission is not based from a particular facility.

BRIEF DESCRIPTION OF THE DRAWINGS

Non-limiting and non-exhaustive embodiments of the present invention, including the preferred embodiment, are described with reference to the following figures, wherein the reference numerals refer to like parts throughout the various view unless otherwise specified.

DETAILED DESCRIPTION

Figure 1:
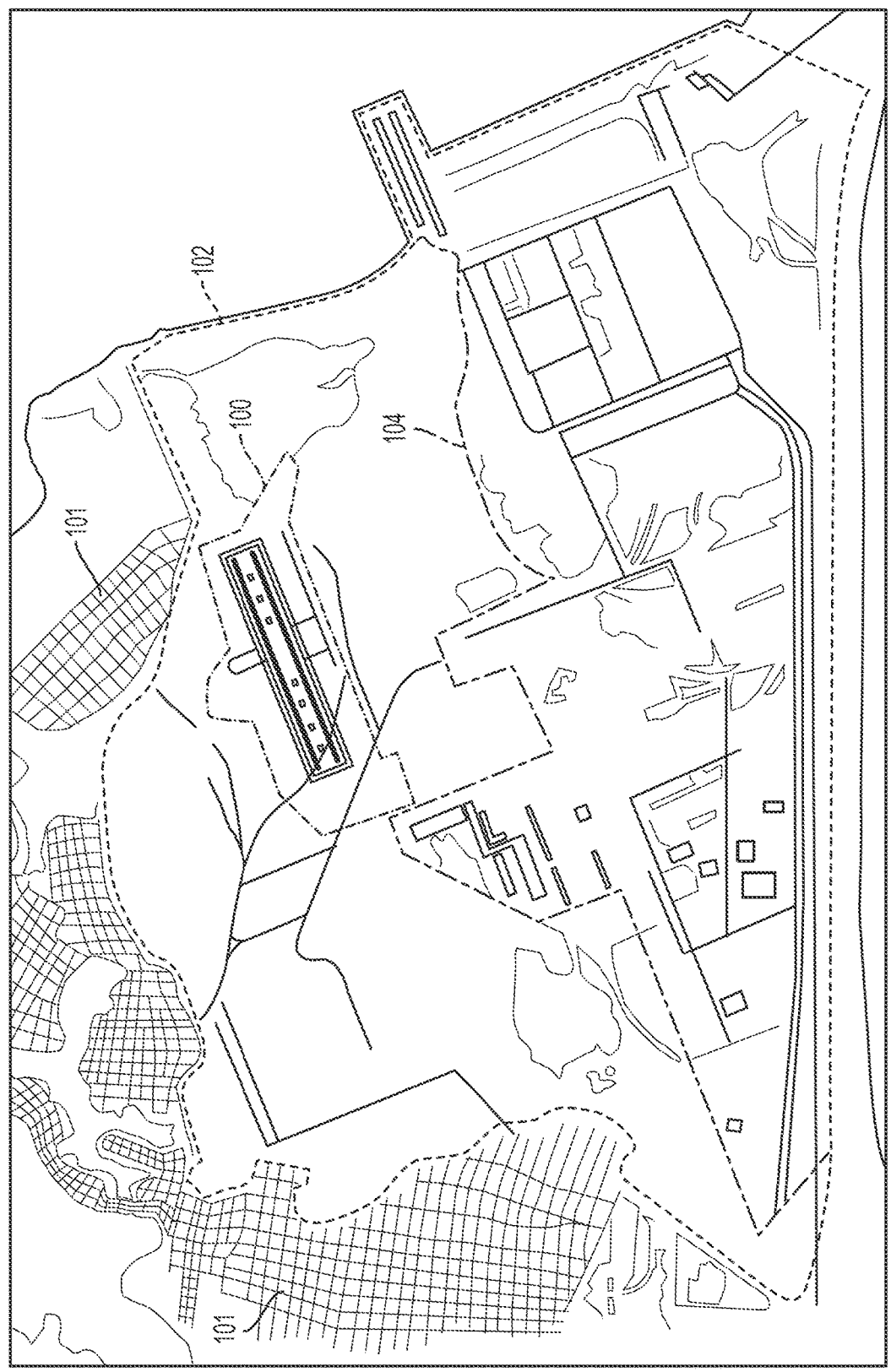
FIG. 1 is an illustration of an industrial park having multiple independent industrial facilities therein, in accordance with an embodiment of the present technology.

The present technology is generally directed to methods and systems for automatically generating a remedial action to facilitate mitigating the effects of one or more undesirable event occurrences in an industrial facility. One aspect of the present technology uses multiple inputs to determine a likelihood of an event occurrence and, based on that likelihood, generate a remedial action. The multiple inputs can be obtained via a plurality of sensors positioned at various points throughout the industrial facility. The one or more of the plurality of sensors can be in communication with one another and be automatically activated based on inputs from other sensors. The inputs of the activating and activated sensors are received via a control system and may be used to determine a likelihood of an undesirable event occurrence. Based on the likelihood of the event occurrence, the control system can automatically generate a remedial action, which can be directed to any source of the undesirable event occurrence. For example, the remedial action can be directed to a secondary source, an environmental source, and/or a process source.

The following table provides potential odor reference descriptions and sources. In accordance with the description herein, one skilled in the art will understand that other industrial, environmental, chemical, and the like, odor descriptions and sources are within the scope of the disclosure.

| Potential Odor Reference | | | |
|---|---|---|---|
| Oder Description | Possible Source | Oder Description | Possible Source |
| Burnt Rubber | Conveyor belt | Rotten Vegetables | Mercaptan/Sulfide |
| Solvent | Ethylbenzene | Exhaust | Gasoline Vehicle |
| Garlic | Dimethyl sulfoxide | Fecal/Feces/Manure | Skatole |
| Metallic Taste, Sharp Imitating | Sulfur Dioxide | Slight Metallic Taste/Burnt Odor | Coke Plant-Heat Recovery |
| Tar Like Smell | Tar | Rotten Egg Sulfur Smell | Coke Plant-Byproduct Plant |
| Mothballs | Naphthalene | Solvents/Tar Slight Metallic Taste/Burnt Odor | |
| Rotten Eggs | Hydrogen sulfide | Vinegar | Acetic Acid |
| Coal-Like Odor | Coal | Sour Milk | Propionic Acid |
| Gasoline | Petroleum Distillation/Gas Station | Arcenatic, Sweet, Solvent | Benzene |
| Diesel Fuel Kerosene/Home Heating Oil | Petroleum Distillation/Gas Station | Metallic | Hot Metals |
| Burnt Wood | Trees/Bush | Nail Polish Remover | Acetone |
| Ammonia-like, Pungent, Imitating | Ammonia | Medicinal Acidic, Creosote | Phenol |
| Skunk-like/rancid | Mercaptans | Natural Gas | Mercaptans |

Specific details of several embodiments of the technology are described below with reference to the Figures. Other details describing well-known structures and systems often associated with pusher systems, charging systems, and coke ovens have not been set forth in the following disclosure to avoid unnecessarily obscuring the description of the various embodiments of the technology. Many of the details, dimensions, angles, spatial orientation and other features shown in the Figures are merely illustrative of particular embodiments of the technology. Accordingly, other embodiments can have other details, dimensions, angles, spatial orientation and features without departing from the spirit or scope of the present technology. A person of ordinary skill in the art, therefore, will accordingly understand that the technology may have other embodiments with additional elements, or the technology may have other embodiments without several of the features shown and described below with reference to the Figures.

FIG. 1 is an illustration of an industrial park 102 and a neighboring public community 101 adjacent the industrial park. The industrial park 102 includes an industrial facility 100 and a secondary industrial facility 104 located near the facility 100. The term "industrial facility" as used herein is meant to be interpreted broadly and include any facility operating a process whereby a raw material is converted to a usable commodity. For example, an industrial facility can include a plant performing coke processing (e.g., heat recovery and/or by-product), coke inventory processing, steel processing, heat recovery, chemical processing, and/or similar operations. An industrial facility can also include any plant having industrial ovens, furnaces, reformers, dryers, stackers, wharf operations, quench towers and similarly related equipment.

The facility 100 can include a plurality of sensors positioned throughout the facility 100 and configured to detect various materials generated from the facility 100 and/or from the secondary industrial facility 104. As described in detail below with reference to FIG. 2, the sensors can be used to determine whether the source of a detected input was likely from the facility 100 or the secondary facility 104. Determining the source of an input can thereby be used to determine a likelihood of an undesirable event occurrence and automatically generate a remedial action to prevent such an event.

Figure 2:
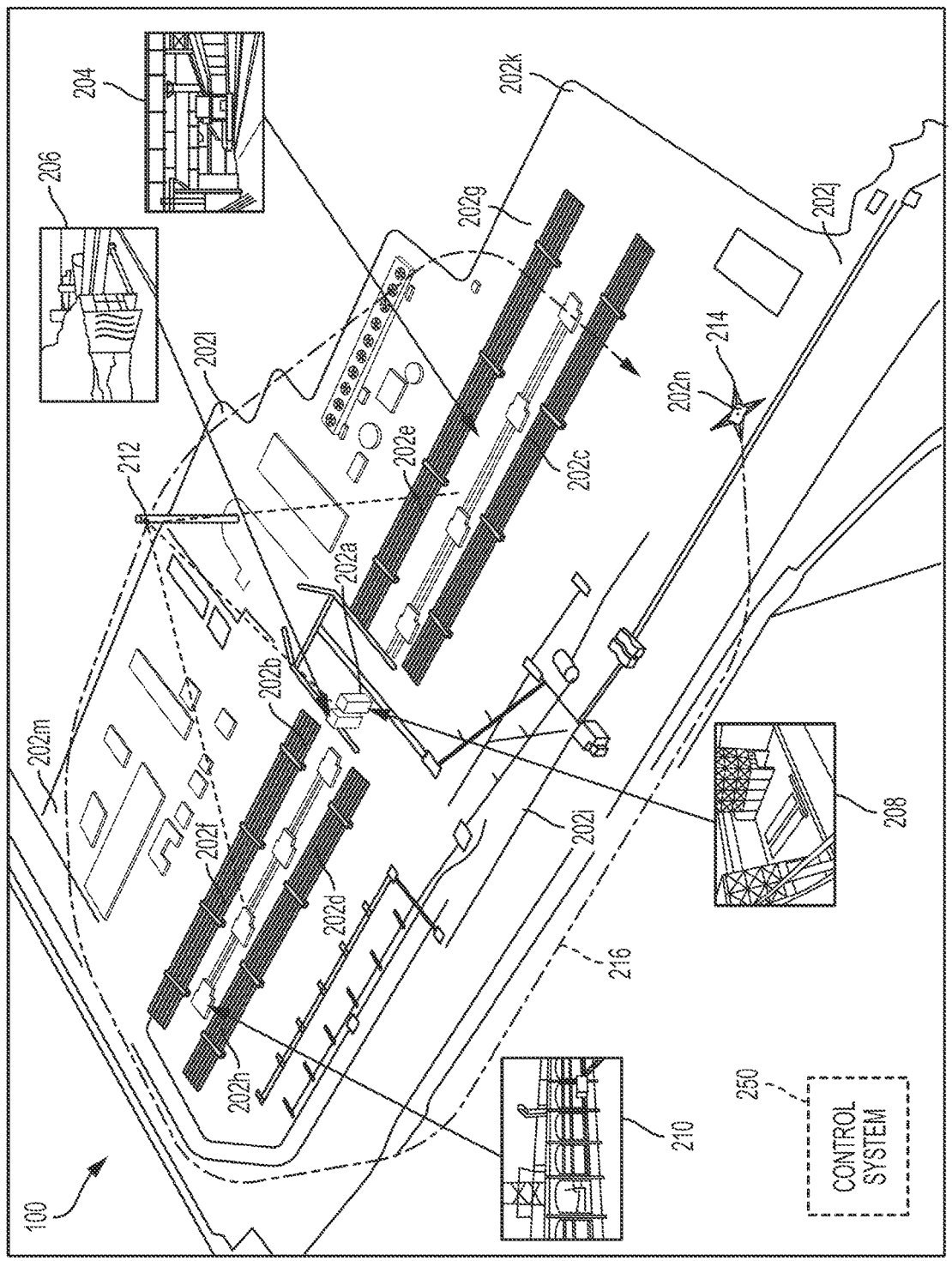
FIG. 2 is an isometric view of the industrial facility shown in FIG. 1, in accordance with an embodiment of the present technology.

FIG. 2 is an isometric view of the facility 100, in accordance with an embodiment of the present technology. The facility 100 includes a plurality of sensors 202 (identified individually as 202a, b, c, d, e, f, g, h, i, j, k, l, m, n) positioned at various points throughout the facility 100. Each individual sensor 202a-n can represent a single sensor or a plurality of different sensors at a single location. For example, individual sensor 202a can correspond to a single sensor that can detect total reduced sulfur (TRS), or a plurality of sensors that can each detect a different chemical and/or material. In some embodiments, the sensors 202 are strategically placed around the facility 100 and may be positioned adjacent particular areas of the facility 100 that commonly generate material gases or chemicals of interest. For example, the embodiment shown in FIG. 2 corresponds to a coke-producing facility and includes areas such as hot car loading 204, quench towers 206, wharfs 208, and coke oven charging/pushing 210. In such an embodiment, the sensors 202 may be positioned adjacent these areas of the facility 100 to ensure that material gases or chemicals generated from these areas are detected. The sensors 202 can each include a positional component and thus can help determine the source of a particular material. For example, when one or more of the sensors detects a material of interest, the operator can identify a likely source of the material based on the sensor reporting the detection and the one or more sensors not reporting a detection. Similarly, the time that a material is detected on a first sensor relative to the time that a material is detected on a second sensor can be indicative of the source of the material and the dispersion pattern for the material. The sensors 202 can also be strategically placed around a facility 100 to determine whether the source of the material of interest is within the facility 100 or external to the facility 100 and from a secondary source (e.g., the secondary facility 104).

The sensors 202 can be used to detect any parameter associated with managing the facility 100. For example, the sensors 202 can detect process parameters (e.g., process temperatures, process pressures, equipment skin temperatures, equipment operating status, opacity, particulate matter, etc.) and/or environmental parameters (wind direction, wind strength, ambient temperature, atmospheric pressure, humidity, rain index, heat index, etc.). The sensors 202 can also include analyzers and be configured to measure a particular material or chemical concentration (ppb) of TRS, organic sulfur, sulfur dioxide ($SO_2$), sulfur trioxide ($SO_3$), hydrogen sulfide ($H_2S$), sulfuric acid ($H_2SO_4$), thiols, nitric oxides (NOx), smog, ozone, volatile organic compounds (VOC), total hydrocarbons, lead, ammonia ($NH_3$), hydrochloric acid (HCl) and/or particulate matter ($PM_{2.5}$ and/or $PM_{10}$). The sensors 202 can also be configured to detect nuisances such as noise levels (e.g., decibels) and/or odor.

The sensors can also include rotatable cameras 212 that use laser, spectroscopic, and/or infrared analysis and are configured to detect, for example, opacity or skin temperatures. The camera 212 can, for example, use pulsed laser light (e.g., LIDAR) and/or differential optical absorption spectroscopy (DOAS).

In some embodiments, a portion of the sensors 202 can be stationary sensors that are relatively permanently fixed while other sensors 202 can be movable. For example, the movable sensors 202 can be attached to movable sources, such as hot cars or operators themselves. In other embodiments, the facility can include one or more unmanned aerial vehicles (e.g., drones) 214 with a sensor (e.g., sensor 202n) attached thereto. As described in more detail below with reference to FIGS. 3 and 4, the drone 214 and/or sensor 202n can be activated and configured to circle the facility 100 along a path 216 to provide additional inputs.

The facility 100 also includes a control system 250 in communication with each of the sensors 202. Amongst other features, the control system 250 is used to receive inputs from the sensors 202 and allows operators to control and/or activate the sensors 202 from a remote location. Many embodiments of the control system 250 and/or technology described below may take the form of computer-executable instructions, including routines executed by a programmer or programmable computer. The control system 250 may, for example, also include a combination of supervisory control and data acquisition (SCADA) systems, distributed control systems (DCS), programmable logic controllers (PLC), control devices, and processors configured to process computer-executable instructions. Those skilled in the relevant art will appreciate that the technology can be practiced on computer systems other than those described herein. The technology can be embodied in a special-purpose computer or data processor that is specifically programmed, configured or constructed to perform one or more of the computer-executable instructions described below. Accordingly, the terms "control system" and "computer" as generally used herein refer to any data processor. Information handled by these computers can be presented at any suitable display medium, including a CRT display or LCD.

Figure 3:
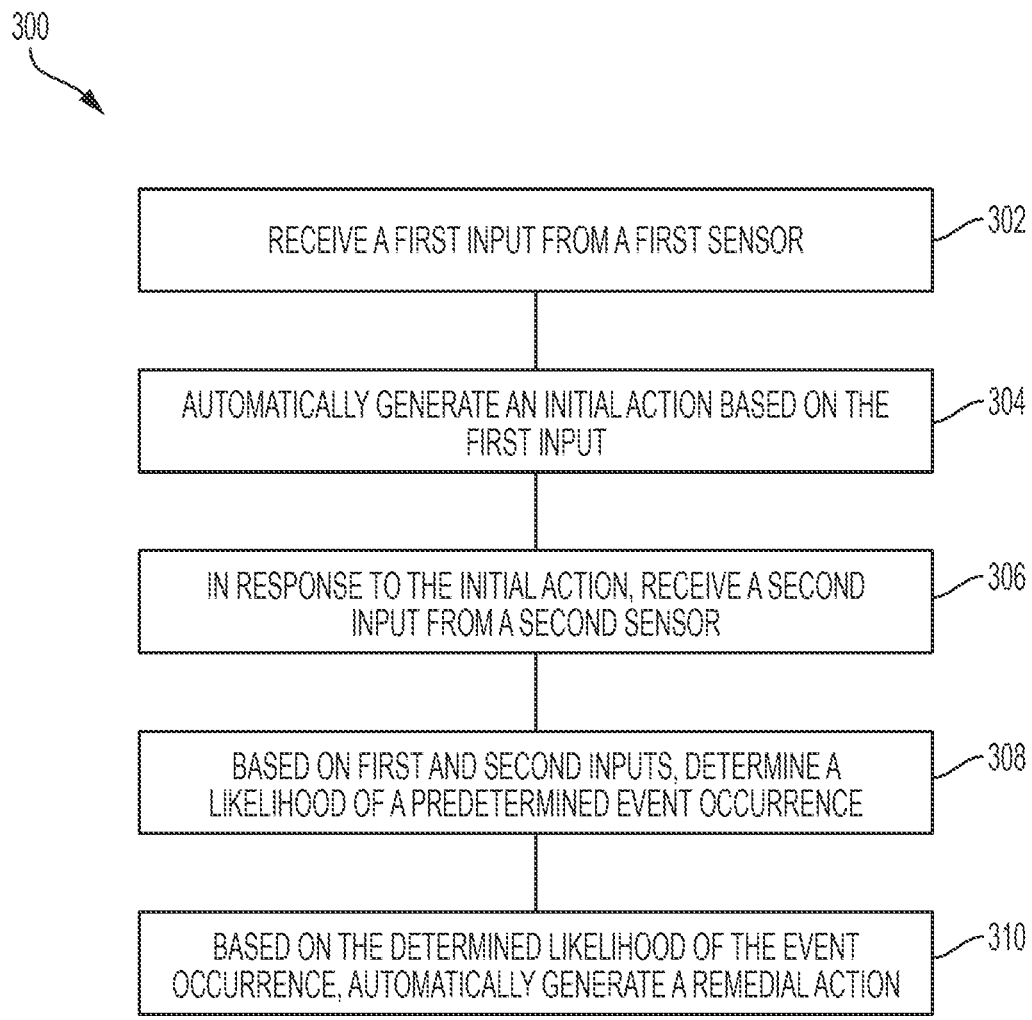
FIG. 3 is a block diagram illustrating a process for automatically generating a remedial action based on a determined likelihood of an event occurrence in an industrial facility, in accordance with an embodiment of the present technology.

FIG. 3 is a block diagram illustrating an overall process 300 for automatically generating a remedial action based on a determined likelihood of an event occurrence in an industrial facility. The overall process 300 includes receiving a first input from a first sensor (block 302). The first sensor can include one or more of any of the sensors 202a-n previously described above with reference to FIG. 2. The first input can include any of the parameters described above with reference to FIG. 2 including the process parameters, environmental parameters, chemical concentrations and/or nuisances. Receiving the first input can be done via the control system 250. Additionally, the first input used by the control system 250 to perform subsequent actions (e.g., to generate an initial action, determine a likelihood of an event occurrence, generate a remedial action, etc.) may be the result of averaging or modal selection (i.e., two out of three voting selection) of one or more inputs. Additionally, the control system 250 may be programmed to use an input only after the input has exceeded a value multiple times. For example, a $H_2S$ concentration of 10 ppb may not be actually used by the control system unless a reading above 10 ppb is received multiple times.

The process 300 further includes automatically generating an initial action based on the first input (block 304). The initial action can include activating one or more second sensors (e.g., one or more of the individual sensors 202a-n and/or camera 212). Activating one or more second sensors as used herein is meant to be interpreted to mean that inputs from those sensors begin to be received and used by the control system 250. Even before a sensor is activated, the control system 250 is capable of receiving the second input and capturing a value of the second input. Until a sensor is activated, though, the control system 250 may not be using the second input to, for example, determine a likelihood of an event occurrence, as explained in further detail below. The initial action can also include activating a separate piece of equipment (e.g., the drone 214) attached to the one or more second sensors. The initial action can also include notifying an operator to take a manual reading including a smell, visual, or hearing indication. For example, for a first input of a detected concentration of $H_2S$ outside a predetermined range, the initial action can include notifying the operator to perform a smell test in a nearby area. In another example, operators who are trained to be method 9 certified (visual opacity) can be notified to perform a visual opacity check and manually input the results into the control system 250.

The process 300 further includes receiving a second input from a second sensor in response to the initial action (block 306). The second sensor can include one or more of any of the sensors 202 previously described above with reference to FIG. 2. The type and processing (e.g., averaging, modal selection, exceeding a value, etc.) of the second inputs can be identical to the first inputs and can include any of the parameters described above with reference to FIG. 2, including the process parameters, environmental parameters, chemical concentrations and/or nuisances. Receiving the second input can be done via the control system 250.

The process 300 further includes determining a likelihood of an undesirable event occurrence based on the first and second inputs received (block 308). As described in further detail below, the likelihood of the event occurrence can be a computer-generated probability and/or an alert level presented to the operator. For example, the likelihood can include two or more levels (e.g., a low level likelihood, a medium level likelihood, and a high level likelihood of occurrence) that help determine whether a remedial action should be taken. The event occurrence can be a complaint for the public community, and/or any process condition (e.g., an equipment shutdown or a process shutdown), nuisance, or environmental condition (e.g., an odor perception) that is the source of the complaint.

Based on the determined likelihood of the event occurrence, the control system 250 can also automatically generate a remedial action (block 310). As such, a first determined likelihood can lead to a first remedial action and a second determined likelihood, different than the first determined likelihood, can lead to a second remedial action, different than the first remedial action. As explained in further detail below with reference to FIGS. 4A and 4B, the remedial action can be directed to decreasing the likelihood of the event occurrence, mitigating one or more effects of the event occurrence, or further understanding the likelihood of the event occurrence. For example, a remedial action may include activating a third sensor to generate a third input to more accurately determine the likelihood of the event occurrence. In such an embodiment, an updated likelihood of the event occurrence is then determined and another remedial action may be automatically generated. The remedial action is also generated in real-time. The term "real-time" as used herein is not to be interpreted as immediately. Instead, the term "real-time" is to be interpreted to mean "without significant delay." In the context used above, the remedial action generated in real-time means that the remedial action is generated before the likelihood of the event occurrence has significantly changed to make the generated remedial action obsolete. Notably, a remedial action in one scenario can be the same as an event occurrence in another scenario. For example, the remedial action is one scenario may be to shutdown a process to stop emitting TRS and prevent the event occurrence of a complaint from the public community. In another scenario, the remedial action may be turn turndown operations to prevent the event occurrence of a shutdown. The remedial action can also include maintaining the process in its current state of operation. For example, if a first input indicates that a particular oven's skin temperature (e.g., a crown temperature) is hotter than normal, the control system 250 may hold the oven in its current state of operation instead of pushing it and proceeding according to the normal procedure.

Figure 4A:
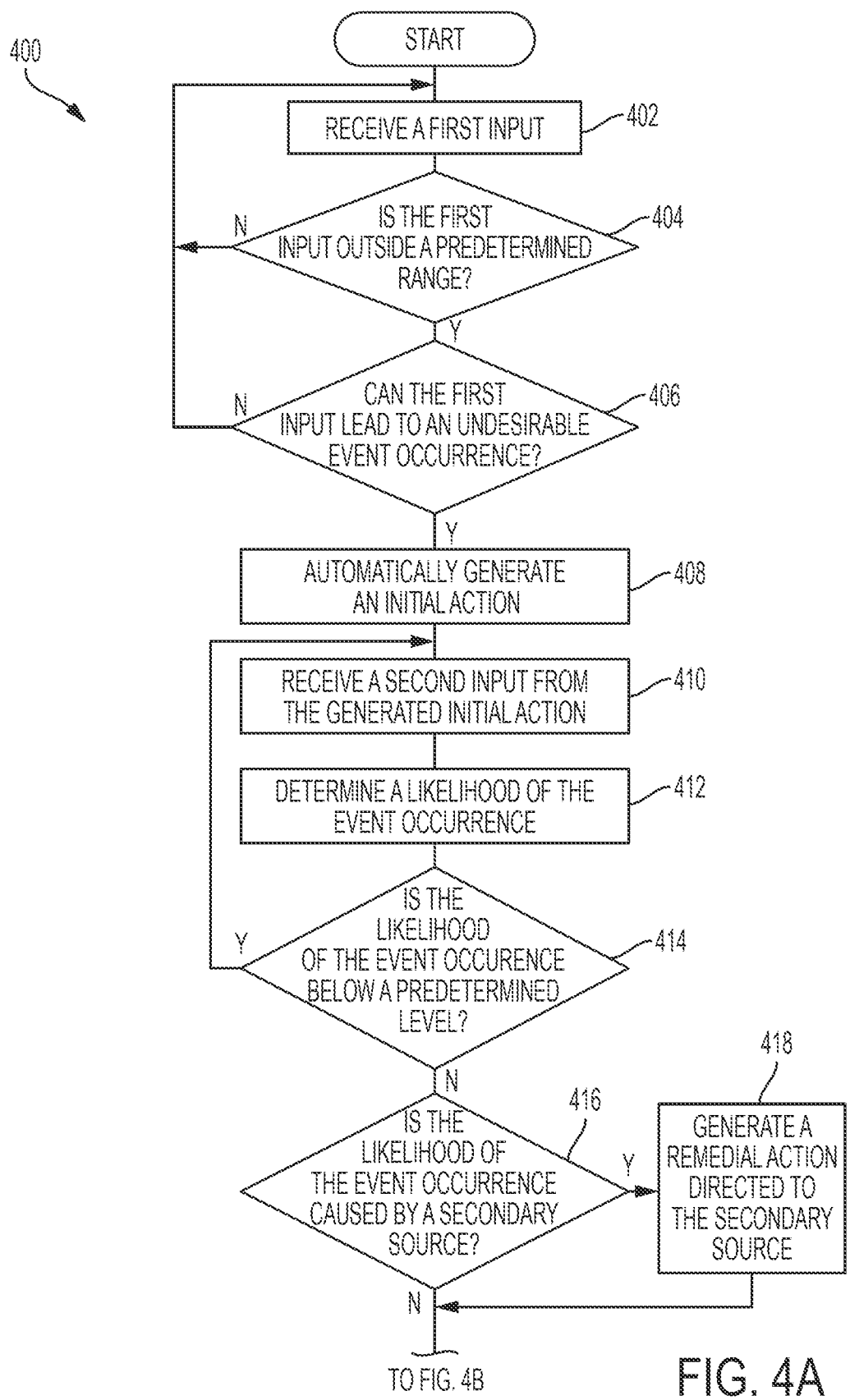
FIGS. 4A and 4B are flowcharts illustrating details for automatically generating a remedial action based on a determined likelihood of an event occurrence in an industrial facility, in accordance with an embodiment of the present technology.
Figure 4B:
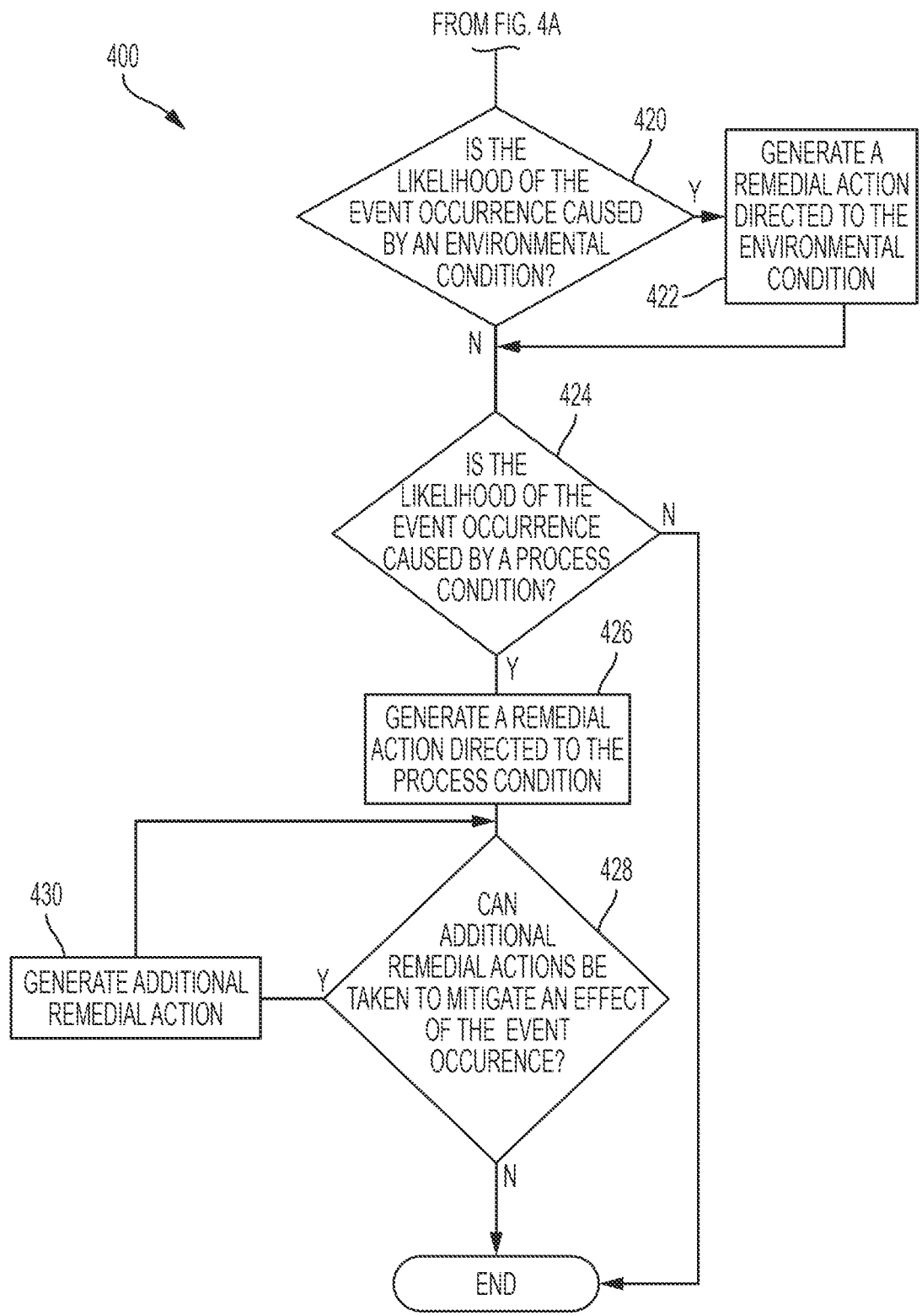

FIGS. 4A and 4B depict a process 400 that includes additional details for automatically generating a remedial action based on a determined likelihood of an event occurrence in an industrial facility. The process 400 includes many identical features and steps to the process 300. For example, the process 400 begins by receiving a first input 402 and determining whether the first input is outside a predetermined range (block 404). If the first input is not outside the predetermined range, the control system 250 can assume that no abnormal condition exists and the process 400 will revert to receiving additional first inputs. If the first input is outside the predetermined range, the control system 250 will then determine whether the first input can lead to an undesirable event occurrence (block 406). Determining whether the first input can lead to an undesirable event occurrence may be based upon how closely linked the first input is to the event occurrence. For example, if the event occurrence is an odor perception of sulfur and the first input is a concentration of $H_2S$ outside the predetermined range, the first input will likely be classed as an input that can lead to the odor perception. If, however, the first input is a wind strength outside a predetermined range, the first input will likely not be classed as an input that can lead to the event occurrence of the sulfur odor perception. As such, the determination of whether an input can lead to a particular undesirable event occurrence is defined for each input. Additionally, since an input can potentially lead to different event occurrences, this determination for each input should be defined for each of the event occurrences.

If the control system 250 determines that the first input does not lead to the event occurrence at issue, the process 400 reverts back to receiving additional first inputs. If the control system 250 determines that the first input can lead to the event occurrence at issue, the process proceeds to automatically generating an initial action (block 406). If, for example, the first input is outside a predetermined range, then an abnormal condition may exist in the facility and the control system 250 may automatically generate the initial action to better understand why the first input is outside the predetermine range. As such, the initial action results in the control system receiving a second input (block 410). The second input from the second sensor can bolster the facility's understanding of why the first input from the first sensor was outside the predetermined range. The control system 250 determines which second sensor provides the second input based on a set of pre-programmed rules. For example, for a first input of a detected concentration of $H_2S$ outside a predetermined range, the control system 250, in some embodiments, may have instructions to receive a second input that facilitates determining the source of the abnormal detected concentration of $H_2S$. In such an embodiment, the received second input may be an operating status of one or more of the equipment (e.g., the furnace, ovens, quench towers, wharf operation, etc.) that operate on an intermittent basis. In other embodiments, the control system 250 may have instructions to receive a second input that facilitates determining whether the first input can lead to other potential issues caused by the first input being outside the predetermined range. In such an embodiment, the received second input may, for example, be a wind direction or wind speed that can cause the first input to disperse to other areas of the facility or areas outside the facility.

Based on the received first and second inputs, the control system 250 then determines a likelihood of the event occurrence (block 412). As previously mentioned, the likelihood of the event occurrence can be an alert level presented to the operator. Determination of the likelihood level can be based upon a set of rules manually programmed into the control system 250. For example, the control system 250 may have instructions to recommend a higher likelihood level of the event occurrence if the first and second inputs are each outside a respective predetermined range and have previously led to the event occurrence. In such an embodiment, the control system 250 may access a database having historical results correlating the specific first input, second input and event occurrence to one another. This database can be automatically updated by the control system after a particular event occurrence does or does not occur. For example, if a particular first input and second input do not lead to an event occurrence, a data point capturing this lack of the event occurrence is stored in the database and can be used to more accurately determine the likelihood of the event occurrence in future similar scenarios.

Once the likelihood of the event occurrence is determined, the control system 250 then determines whether the likelihood is below a predetermined level (block 414). The predetermined level can be manually set for each event occurrence, and may be based on the effect of the event occurrence. If the effect of the event occurrence is a process shutdown, which may result in significant amounts of downtime, then the predetermined level will be relatively low to ensure that an action is taken to prevent the event occurrence or mitigate the effect of the event occurrence. If, however, the effect of the event occurrence is relatively minor, then the predetermined level will be relatively high so that unnecessary remedial actions are avoided. If the likelihood of the event occurrence is below the predetermined level, the process 400 reverts back to receiving additional second inputs. If the likelihood of the event occurrence is not below the predetermined level, the process 400 then determines the cause of the likelihood.

The process 400 next determines whether the likelihood of the event occurrence is caused by a secondary source. A secondary source includes any chemical, material or condition not generated by the facility 100. Referring back to FIG. 1, any material generated from the secondary facility 104 would be considered a secondary source. For example, a nearby oil refinery or a train or truck that is transporting a product can be a secondary source. In such an example, sensors that detect an input from the secondary source can immediately determine whether the source of the detected input is secondary based on other inputs, such as whether any sources within the facility 100 that could generate that input are in fact operating. If the determined likelihood of the event occurrence is at least partially caused by the secondary source, then a remedial action directed to the secondary source is generated. As an example, this type of remedial action can include automatically notifying the secondary facility 104 that a material generated from the secondary facility 104 was detected. In another example, the remedial action can include automatically notifying a local regulatory agency or public community 101 that a material has been detected, but that the facility 100 is not the source of the material.

Once the remedial action is generated or if the control system 250 determines that the likelihood of the event occurrence is not caused by a secondary source, the process 400 proceeds to determine whether the likelihood of the event occurrence is caused by an environmental condition (block 420). An environmental condition can include any condition caused within the facility 100 and by a non-process condition, such as, for example a hazardous chemical spill or emission of hazardous materials. If the control system 250 determines that the likelihood of the event occurrence is at least partially caused by the environmental condition, the control system 250 can automatically generate a remedial action directed to decreasing the likelihood of the event occurrence or mitigating the effect of the event occurrence caused by the environmental condition. For example, if the first input is a $H_2S$ concentration and the second input is a high wind strength, and the environmental condition is a hazardous chemical spill, any effect of the chemical spill could be mitigated by limiting any further chemical spill, containing the spill, and safely cleaning up the chemical spill as soon as possible to ensure the spill does not cause injury to personnel. As such, the remedial action could be to notify all personnel to stay away from that particular area, and provide detailed instructions according to company protocol to safely clean up the spill. Notably, the remedial action can be generated in real-time because it is automatic.

Once the remedial action is generated or if the control system 250 determines that the likelihood of the event occurrence is not caused by an environmental condition, the process 400 proceeds to determine whether the likelihood of the event occurrence is caused by a process condition (block 424). The process condition can include any condition related to the production, distribution or processing of used raw material used to produce and end-product. For example, in a coking facility, the process condition can include, for example, quenching, transporting coke via rail car, wharf operations, etc. If the control system 250 determines that the likelihood is at least partially caused by a process condition, the control system 250 can automatically generate a remedial action directed to decreasing the likelihood of the event occurrence caused by the process condition and/or mitigating the effect of the process condition. For example, if the first input is a $H_2S$ concentration, the second input is a high wind strength, and the process condition includes quenching, the control system 250 can decrease the likelihood of an event occurrence (e.g., odor perception) by generating a remedial action directed toward the quenching (e.g., ceasing the quenching operation).

The process 400 further includes determining whether additional remedial actions can be taken to mitigate or further mitigate an effect of the event occurrence (block 428). If, for example, control system 250 identifies remedial actions other than those already taken that can further mitigate one or more effects of the event occurrence, the control system 250 can generate those additional remedial actions (block 430). This process loop of identifying additional remedial actions continues until the control system 250 determines that no additional remedial actions can be taken to mitigate effects of the event occurrence.

In use, the process 400 over time gathers inputs throughout the facility 100 from various operating times and parameters and can create correlations between inputs and undesirable event occurrences (e.g., complaints from the public community). For example, the control system 250 may, after months or years of operating a facility, determine that there is a strong correlation between wind direction and complaints, and therefore may affect the rates at which a facility 100 operates during particular wind direction to decrease event occurrences. Similar correlations may be determined, for example, between wharf events and complaints. More specifically, correlations between complaints and specific aspects of wharf events, such as when hot spots, smoke and/or flames, may also be determined. In other embodiments, there may be a positive correlations between complaints and ambient temperature (i.e., more complaints as temperature rises) due to more people being outside or open windows. During this time, the facility 100 may choose to turn down operations or be more sensitive to inputs being outside a predetermined range. These correlations will be different for each facility depending on the location of the facility, location of equipment within the facility (e.g., relative to the public community), operating parameters (e.g., process temperatures), and environmental parameters (e.g., wind direction and wind speed). A feature, therefore, of the present technology is to identify correlations between various inputs and undesirable event occurrences to help the particular facility 100 better predict the likelihood of the event occurrences before they occur.

Figure 5:
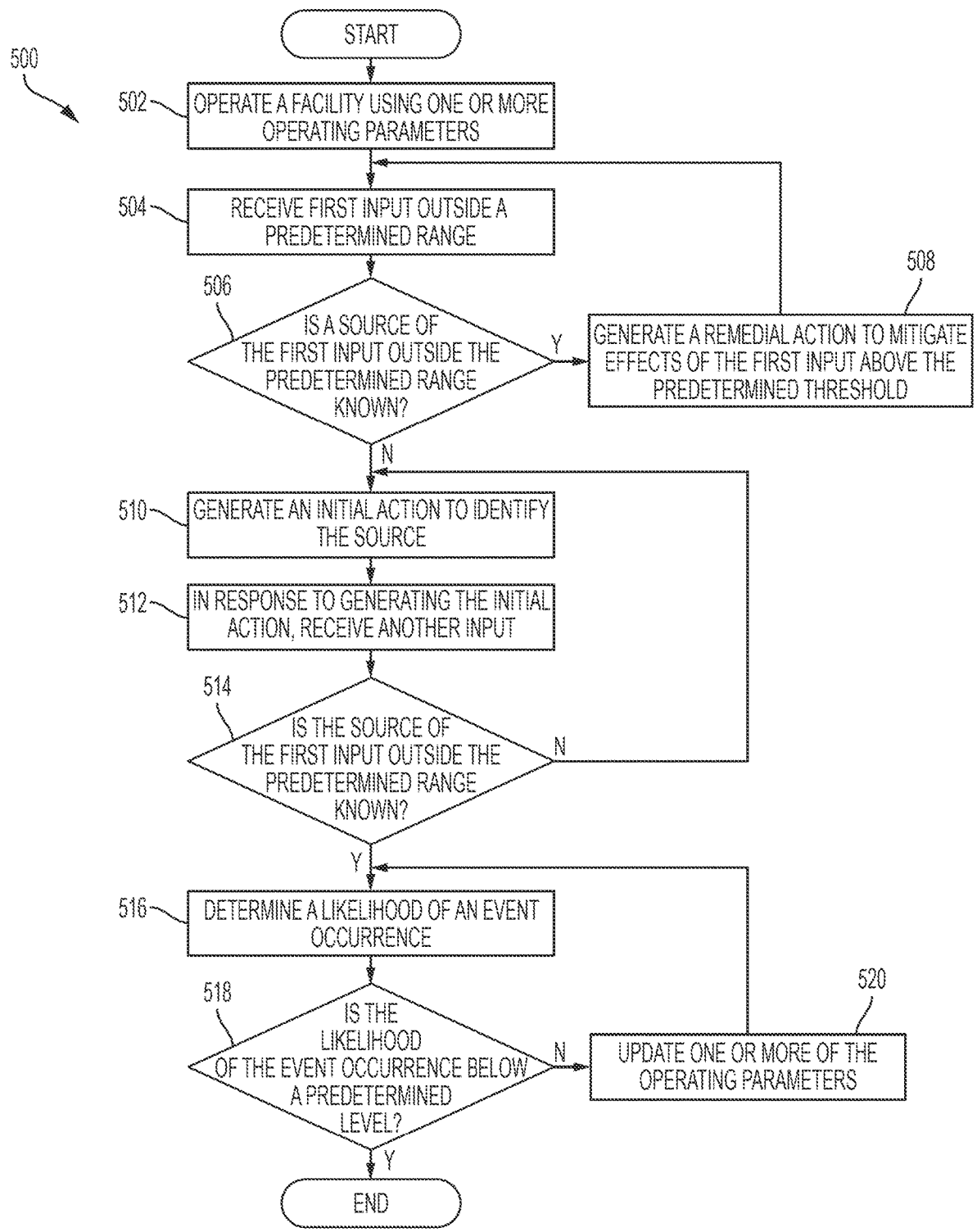
FIG. 5 is a flowchart illustrating details for automatically updating operating parameters used to operate an industrial facility, in accordance with an embodiment of the present technology.

An aspect of the present technology is to react to first and second inputs being outside a predetermined range and based on those first and second inputs, automatically predict the likelihood of an undesirable event before it actually occurs. Referring next to FIG. 5, process 500 illustrates a method to proactively decrease the likelihood of an event occurrence by automatically updating one or more of the operating parameters used to operate the plant. The process 500 begins by operating a facility (e.g., facility 100) using one or more operating parameters (block 502). Assuming the facility 100 and process are in a general steady state, the process 500 receives a first input outside a predetermined range (block 504). In order for the control system 250 to update one or more of the operating parameters, it is helpful to understand the source that caused the first input to be outside the predetermined range. If the source is already known, the control system 250 can generate a remedial action directed to the known source that caused the first input to be outside the predetermined range. If the source is not known, the control system 250 can generate an initial action to identify the source that caused the first input to be outside the predetermined range (block 510). As previously mentioned, this initial action can include activating a second sensor, which in turn can generate another input (e.g., a second input) received by the control system (block 512). Based on the received first and second inputs, the control system 250 again determines whether the source that caused the first input to be outside the predetermined range is known (block 514). If the source is known, the control system 250 can determine a likelihood of an event occurrence (block 516). Similar to the process 400 described above with reference to FIG. 4, the control system 250 then determines whether the likelihood of the event occurrence is below a predetermined level. If the likelihood is below the predetermined level, the control loop ends and the one or more operating parameters do not need to be updated. If the likelihood is not below the predetermined level, then the one or more operating parameters is updated (block 520) and the process 500 reverts to re-determining the likelihood of an event occurrence, which has changed in response to the one or more operating parameters being updated.

Figure 6:
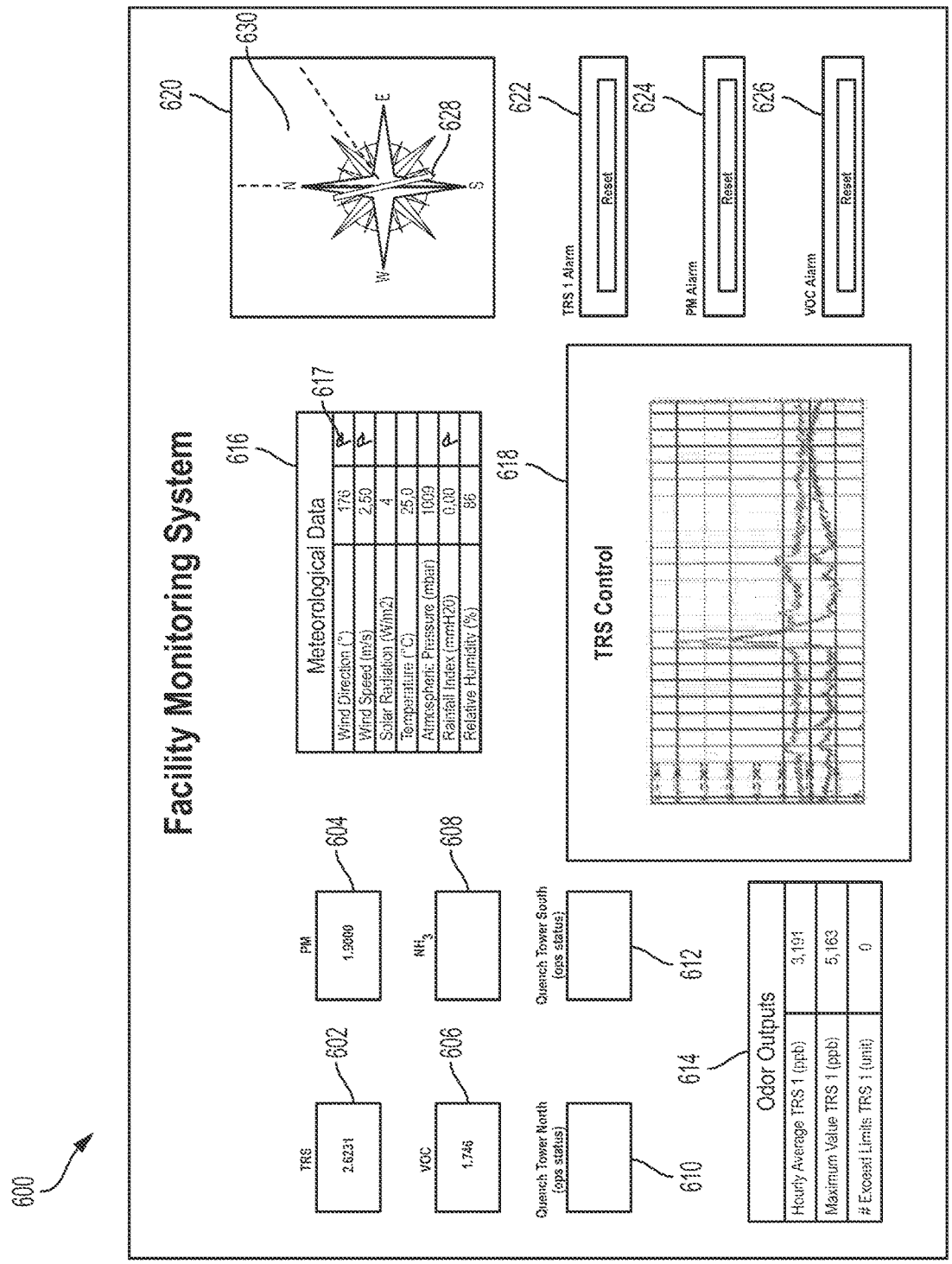
FIG. 6 is a screenshot of a facility monitoring system, in accordance with an embodiment of the present technology.

FIG. 6 is a screenshot of a facility monitoring system 600, in accordance with an embodiment of the present technology. The facility monitoring system 600 displays various inputs received by the control system 250 to, for example, the operator. The facility monitoring system 600 can include inputs for TRS, PM, VOC, $NH_3$, and an operations status for facility equipment (e.g., quench tower north (ops status) 610 and quench tower south (ops status) 612). Each of these inputs corresponds to one or more sensors in the field and includes predetermined alarm limits (e.g., TRS Alarm 622, PM Alarm 624 and VOC Alarm 626) that activate when the one or more inputs read outside a predetermined range. The facility monitoring system 600 also includes a meteorological data chart 616 that includes parameters such as wind direction, wind speed, solar radiation temperature atmospheric pressure, rainfall index, and relative humidity. Those parameters with values outside a predetermined range are flagged with an indication 617. In some embodiments, these indications will only be present if after a first input is received that is outside a predetermined range. In the embodiment shown in FIG. 6, the monitoring system 600 can also include an odor outputs table 614 with inputs including hourly averages, maximum and minimum values of TRS, and the number of times a predetermined limit was exceeded in a set amount of time. Monitoring hourly averages and the number of times a predetermined limit was exceeded creates a more reliable data point for the control system 250 and operators to use to predict the likelihood of an event occurrence. The facility monitoring system 600 can also include trending data via schematic representations of sensor inputs. For example, the embodiment shown in FIG. 6 includes a TRS control chart 618 that corresponds to the TRS input 602. In some embodiments, the operator can click on the different input boxes and the control system 250 will display trending data for the selected input via the schematic representation. The embodiment shown in FIG. 6 also includes a meteorological schematic representation 620 generally corresponding to the meteorological data 616. For example, the schematic representation includes wind direction, represented by the direction of the arrow 628, and wind speed, represented by the length of the arrow 628 (the length of the arrow 628 decreases as wind speed decreases and increases as the wind speed increases). The schematic representation can also include a positional representation of one or more sensors 630 having inputs outside a predetermined range. In the embodiment shown in FIG. 6, the positional representation of the one or more sensor 630 is in the north-east area of the facility 100.

Figure 7:
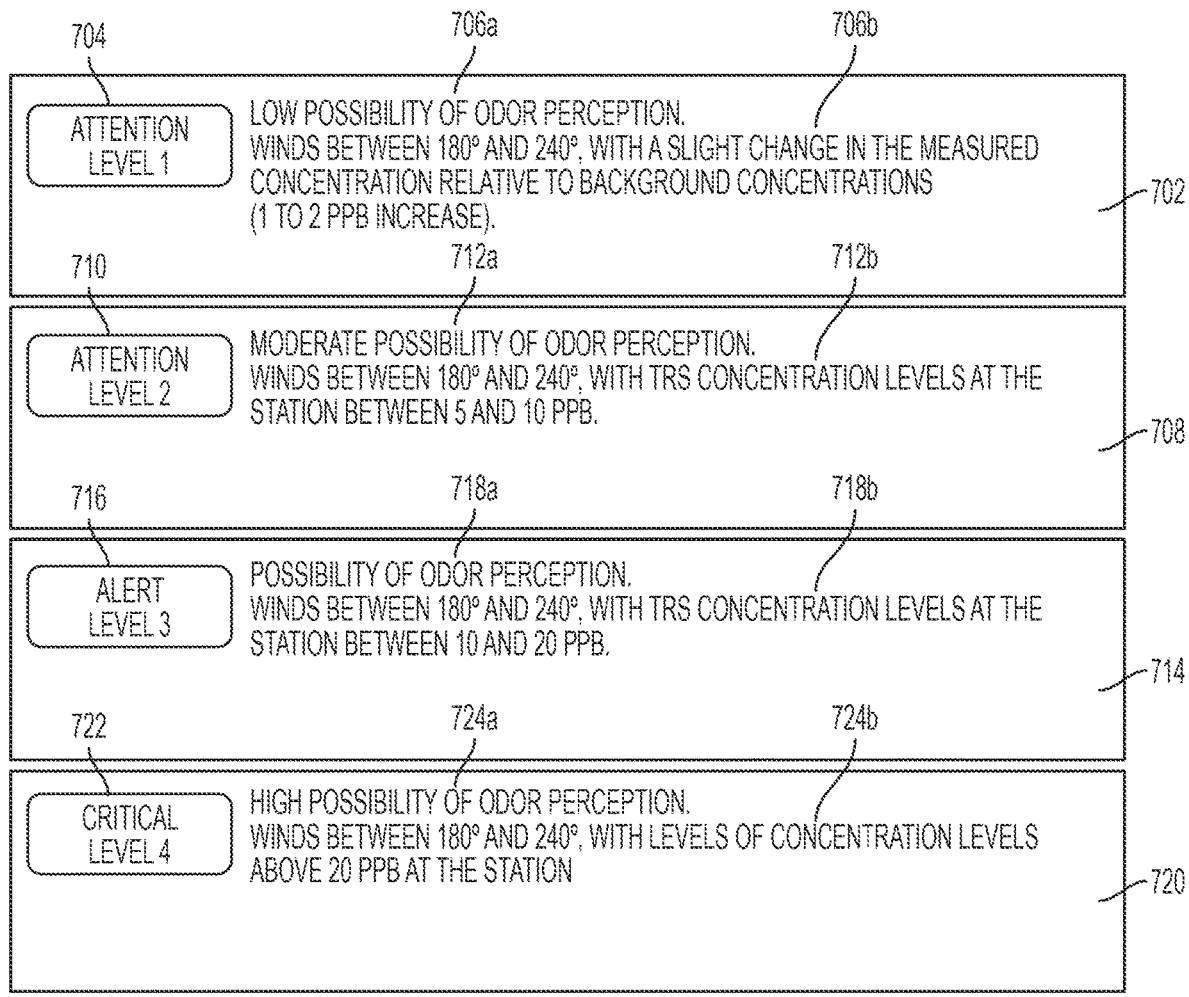
FIG. 7 is a screenshot of alerts displayed to an operator, in accordance with an embodiment of the present technology.

FIG. 7 is a screenshot of different level alerts displayed to an operator on the facility monitoring system. As described earlier with reference to FIG. 3, the likelihood of an event occurrence can be a computer-generated probability and/or an alert level presented to the operator. The embodiment shown in FIG. 7 multiple levels (i.e., degrees) of alarm levels that represent different likelihoods of an event occurrence. For example, the different levels can include an "Attention—Level 1" alarm 702, an "Attention—Level 2" alarm 706, an "Alert—Level 3" alarm 714, and a "Critical—Level 4" alarm 720. Each alarm 702, 708, 714, 720 includes a visual indication of the alarm level (i.e., 704, 710, 716, 722), a description the includes the likelihood of an event occurrence (i.e., 706*a*, 712*a*, 718*a*, 724*a*), and details of the inputs explaining why the likelihood was generated (i.e., 706*b*, 712*b*, 718*b*, 724*b*). For example, the low likelihood 706*a* for alarm level-1 702 was generated because wind direction was between 130-170° and there was a measured TRS concentration of 1-2 ppb above the baseline. As another example, the high likelihood 724*a* for alarm level-4 720 was generated because wind direction was between 180-240° and there was a measured TRS concentration above 20 ppb. In this embodiment, the wind direction between 180-240° may be significant because the public community (i.e., public community 101) is located in this direction.

Figure 8:
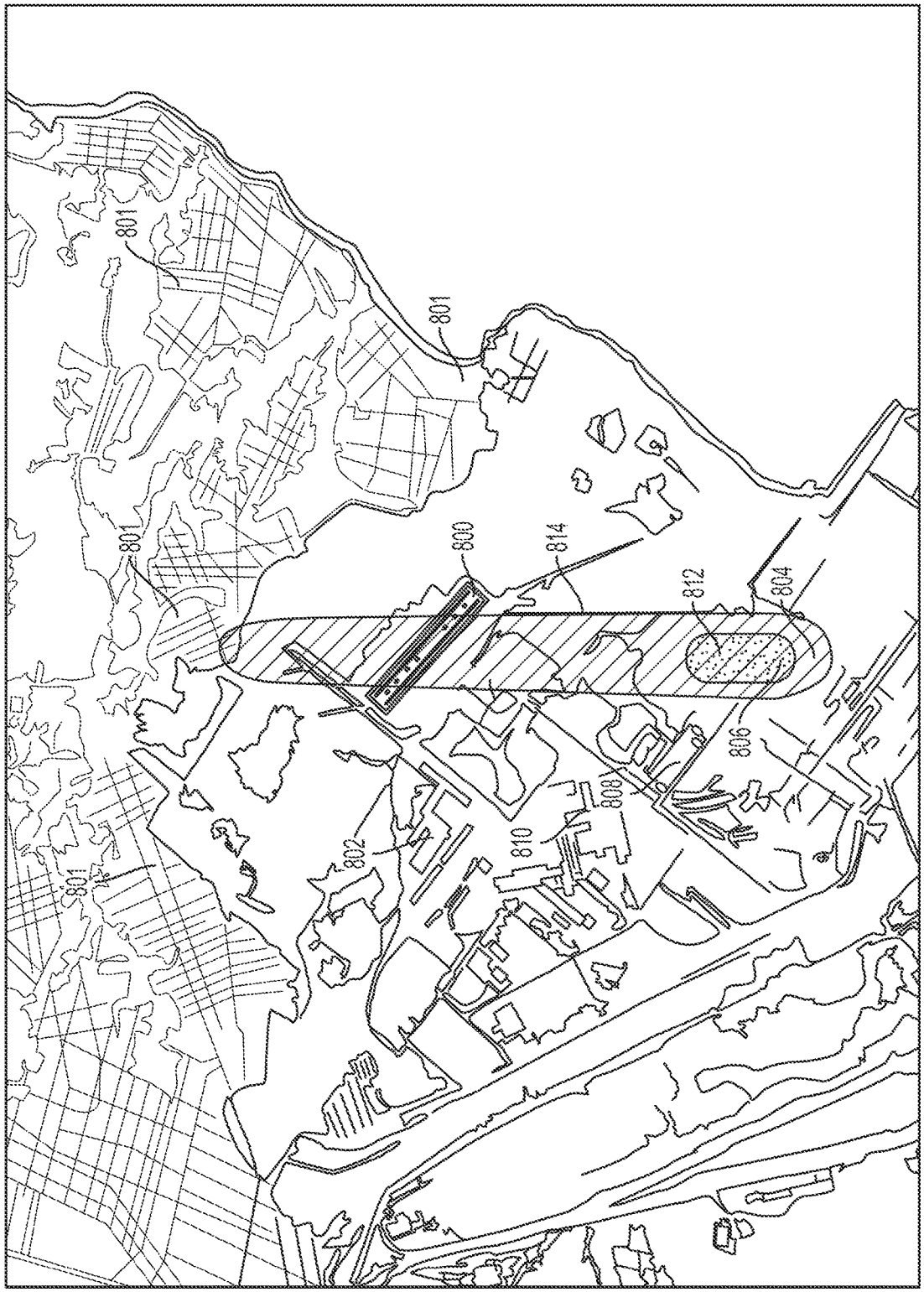
FIG. 8 is an illustration of an industrial park and a predictive model of a dispersion from a secondary source, in accordance with an embodiment of the present technology.

FIG. 8 is an illustration of an industrial park 802 and a predictive model of a material dispersion from a secondary source, in accordance with an embodiment of the present technology. The industrial park 802 can correspond to the industrial park 102 described with reference to FIG. 1. The industrial park 802 includes an industrial facility 800, a neighboring public community 801, as well as multiple sources 802, 804, 806, 808, 810 not within the industrial facility 800. Each of the sources 802, 804, 806, 808, 810 can each generate an emission capable of migrating over the industrial facility 800. As shown in the embodiment of FIG. 8, a plume of material 804 can form from the source (i.e., 802, 804, 806, 808, 810) and slowly disperse towards other areas of the industrial park 802 depending on various factors, such as, for example, wind speed and/or wind direction. A computer-based image of an estimated dispersion 814 of the material gas can be generated and displayed to an operator. The estimated dispersion 814 can help determine a likelihood of an event occurrence, such as a complaint from a member of the neighboring community. The control system 250 may use the data associated with the estimated dispersion 814 to determine what, if any, remedial action to take. In such an example, the remedial action may be to notify the neighboring community that a plume 812 has been released within the industrial park 802. The remedial action may also include notifying the neighboring community 101 that the industrial facility 800 is not the source of plume 812. As such, the control system 250 can decrease the likelihood of the event occurrence (i.e., the complaint from the neighboring community) by automatically generating the remedial action (i.e., notifying the neighboring community 801) in response to first and second inputs (i.e., a detected $H_2S$ concentration, wind speed, wind direction, etc.).

Figure 9:
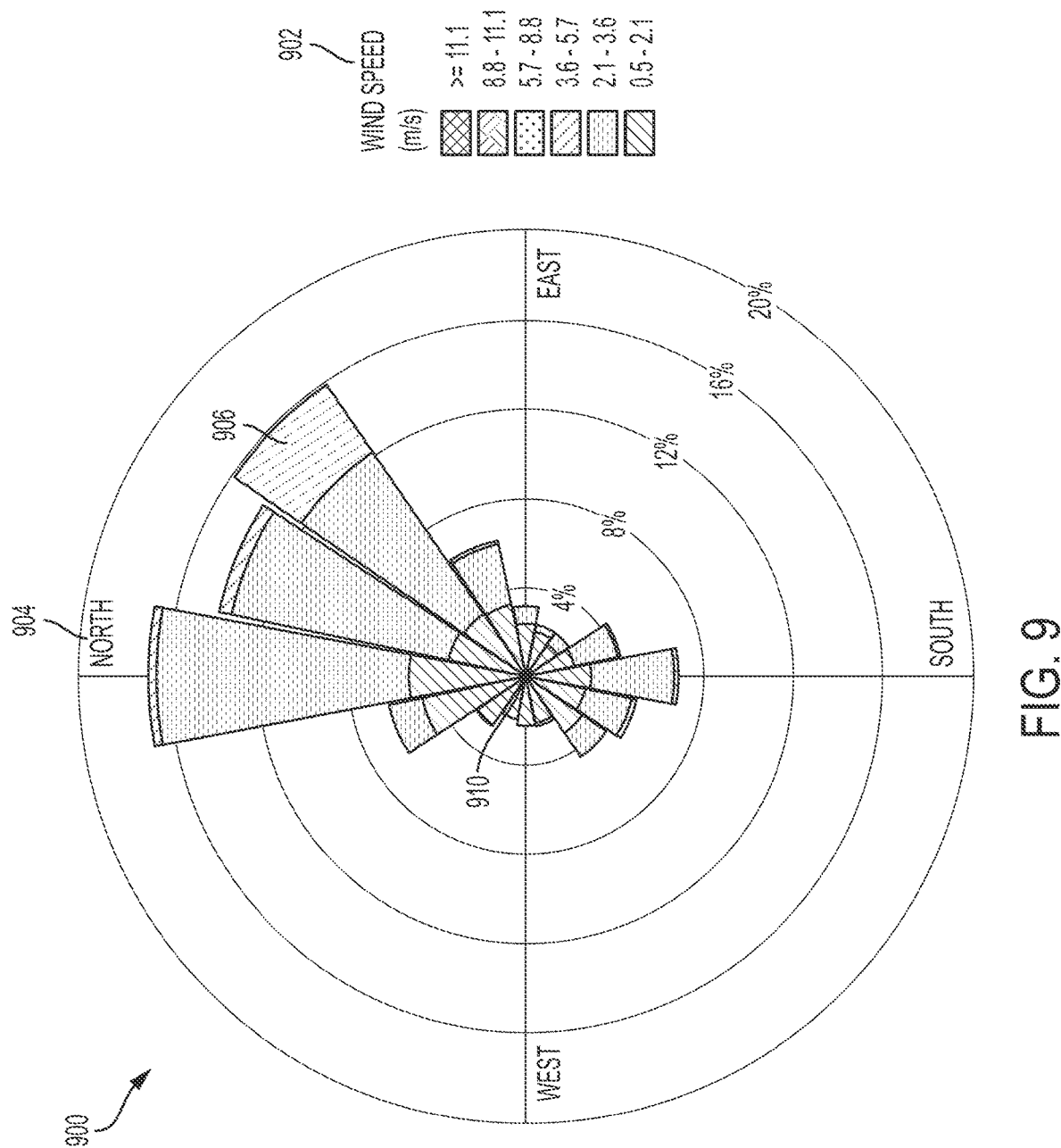
FIG. 9 is a schematic diagram predicting a material dispersion based on wind speed and wind direction, in accordance with an embodiment of the present technology.

FIG. 9 is a wind rose 900 correlating wind speed 902 and wind direction 904 over a set period of time (e.g., one month, one year, etc.). The wind rose 900 can be used to facilitate determining likelihoods of event occurrences, as previously described. The wind rose 900 includes a wind portion 906 indicating that approximately 16% of the wind experienced at a station 910 was in the direct north-east direction. More specifically, approximately 2-3% of the wind was in the north-east direction at wind speeds of 0.5-2.1 m/s, approximately 9% of the wind was in the north-east direction at wind speeds of 2.1-3.6 m/s, and approximately 4% of the wind was in the north-east direction at wind speeds of 3.6-5.7. This data creates a historical result for wind speed and wind direction that can be used to generate more accurate predictive models. For example, wind roses for June 2017, June 2016 and June 2015 can be used to generate predictive models for June 2018. In use, these predictive models can then be used to better predict likelihoods of undesirable event occurrences and take remedial actions to prevent the event occurrences. While the predictive model shown in FIG. 9 is for wind direction and wind speed, similar predictive models can be generated for any other of the environmental or process parameters described herein.

Figure 10:
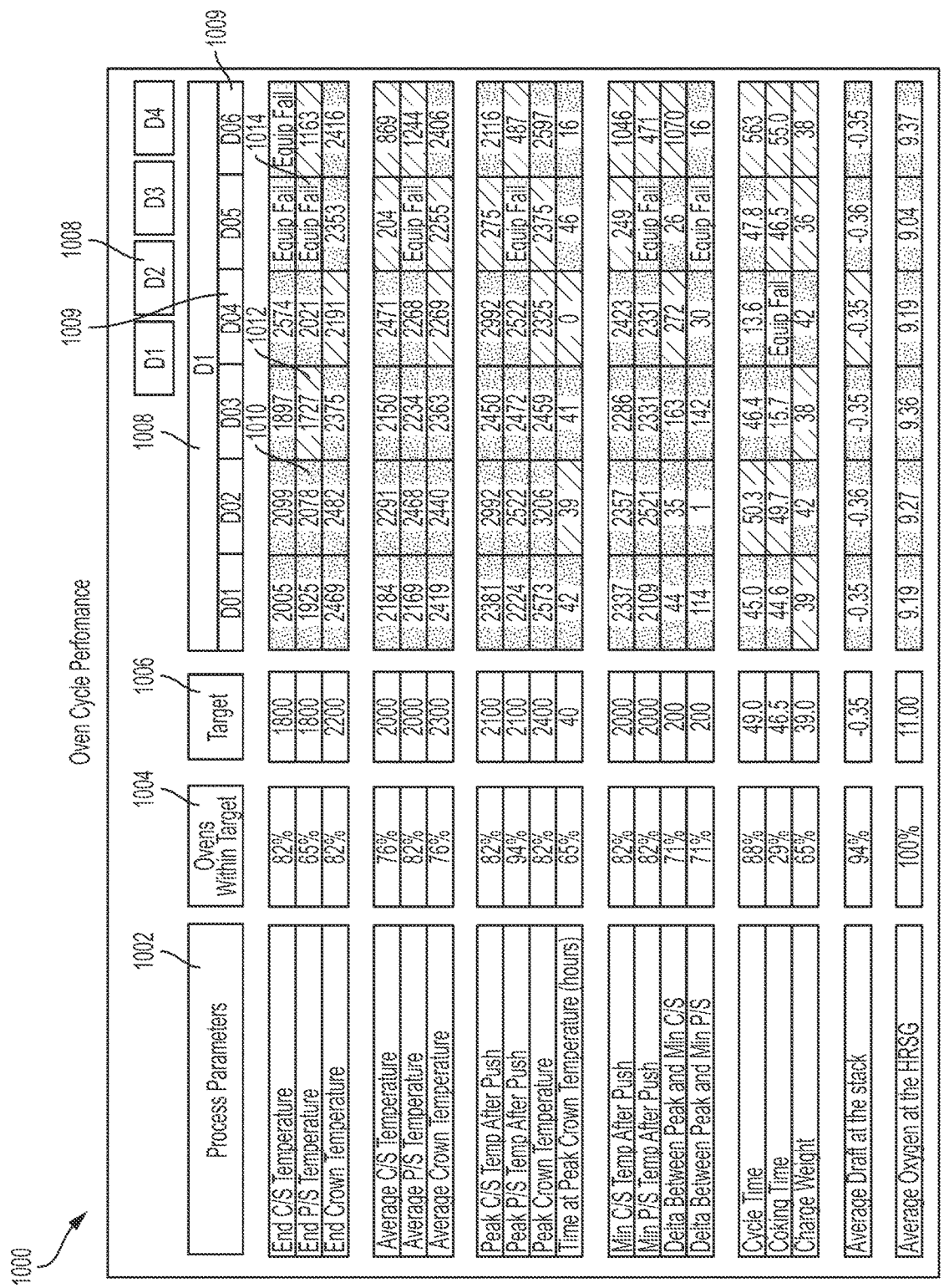
FIG. 10 is a screenshot of oven cycle performance for a coke processing facility, in accordance with an embodiment of the present technology.

FIG. 10 is a screenshot of an oven cycle performance chart 1000 of the facility 100, in accordance with an embodiment of the present technology. The oven cycle performance chart 1000 includes process parameters 1002 and inputs for individual ovens 1008 of a particular bank of ovens 1009. The inputs for each oven 1008 can include temperatures, cycle time, coke time, charge weight, average drafts and average oxygen. Each of these inputs is compared to baseline or target values 1006. The chart 1000 also includes a percentage of ovens within the target value 1004 for each process parameter 1002. Each input of the chart 1000 is shaded according to whether it is meeting the target value, exceeding or not exceeding the target value, or is experiencing an "equipment failure." For example, for the "End Pusher Side Temperature" process parameter, a first input 1010 is meeting the target value of 1800° F., a second input 1012 is not meeting or exceeding the target value of 1800° F., and a third input 1014 is experiencing an "equipment failure."

In use, the oven cycle performance provides the operator with a visual snapshot of how well the overall process and individual ovens are performing. The inputs captured by the oven cycle performance chart 1000 can also serve as the first and second inputs, as described above, and be used to generate likelihoods of event occurrences and remedial actions. For example, an input that is not meeting or exceeding a target value (e.g., second input 1012) or is experiencing a failure (e.g., third input 1014) are often leading indicators that odor, smoke (i.e., opacity), and PM may soon become an issue. As such, these inputs (e.g., second input 1012, third input 1014, etc.) may act as first inputs for the process 300, process 400, and/or process 500 described above. Based on these first inputs, the control system 250 may activate second sensors (e.g., one or more of 202a-n) and receive one or more second inputs to facilitate determining a likelihood of an event occurrence and generating a remedial action.

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

EXAMPLES

The following examples are illustrative of several embodiments of the present technology:

1. A method of mitigating effects of an undesirable event occurrence in an industrial facility, the method comprising:
    receiving a first input from a first sensor;
    based at least in part on the first input, automatically generating an initial action;
    in response to the initial action, receiving a second input from a second sensor;
    based at least in part on the received first and second inputs, determining a likelihood of an undesirable event occurrence; and
    based at least in part on the determined likelihood of the event occurrence, automatically generating a remedial action to mitigate an effect of the event occurrence.

2. The method of claim 1 wherein automatically generating a remedial action includes altering a process parameter of an operating process in an industrial facility.

3. The method of claim 2 wherein altering the process parameter includes at least one of maintaining an operating process or shutting down an operating process.

4. The method of claim 1 wherein generating the remedial action is done in real-time.

5. The method of claim 1 wherein the first sensor includes a first set of sensors and the second sensor includes a second set of sensors.

6. The method of claim 1 wherein automatically generating a remedial action includes activating a third sensor configured to generate a third input, the method further comprising:
    receiving the third input from the third sensor; and
    updating the previously determined likelihood of the event occurrence.

7. The method of claim 6 wherein the remedial action is a first remedial action, the method further comprising:
    based at least in part on the updated likelihood of the event occurrence, automatically generating a second remedial action to mitigate the effect of the event occurrence.

8. The method of claim 1 wherein automatically generating an initial action includes activating the second sensor.

9. The method of claim 1 wherein determining a likelihood of an event occurrence includes generating a visual representation that estimates the effect of the event occurrence.

10. The method of claim 1 wherein receiving a first input includes receiving the first input of a concentration of at least one of sulfur dioxide ($SO_2$), sulfur trioxide ($SO_3$), organic sulfur, sulfuric acid ($H_2SO_4$), hydrogen sulfide ($H_2S$), thiol, nitric oxide (NO), nitric dioxide ($NO_2$), smog, ozone, volatile organic compound (VOC), total hydrocarbons, ammonia ($NH_3$), and/or hydrochloric acid (HCl).

11. The method of claim 1 wherein at least one of the first or second sensors is a particulate matter sensor.

12. The method of claim 1 wherein receiving a first input includes receiving the first input of a nuisance including an audible noise.

13. The method of claim 1 wherein the second input includes an odor measurement.

14. The method of claim 1 wherein receiving a second input includes receiving the second input of at least one of an environmental parameter or a process parameter.

15. The method of claim 14 wherein the environmental parameter includes at least one of a wind direction, a wind strength, an ambient temperature, an atmospheric pressure, a humidity, a rain index, or a heat index.

16. The method of claim 13 wherein the process parameter includes at least one of a process temperature, an equipment skin temperature, a process pressure, an opacity measurement, equipment operating status, or an oxygen concentration.

17. The method of claim 13 wherein the second input is of a process parameter received from a camera system using at least one of laser, spectroscopy, or infrared analysis.

18. The method of claim 1, further comprising:
receiving a third input of a secondary source external to the industrial facility; and
determining an impact of the secondary source on the likelihood of the event occurrence.

19. The method of claim 1 wherein the first sensor and second sensor are in communication with one another.

20. The method of claim 1 wherein determining a likelihood of an event occurrence includes accessing a database having information of previous event occurrences and corresponding first and second inputs.

21. The method of claim 1 wherein the likelihood of the event occurrence includes at least a first likelihood and a second likelihood and the remedial action includes at least a first remedial action and a second remedial action different than the first remedial action, and wherein the first likelihood generates the first remedial action and the second likelihood generates the second remedial action.

22. A system comprising:
a first sensor in an industrial facility;
a second sensor in the industrial facility; and
a programmer in communication with the first and second sensors and having a computer-readable medium with instructions that, when executed, is configured to:
receive a first input from the first sensor;
based at least on the first input, automatically generate an initial action to facilitate determining a likelihood of an event occurrence;
receive a second input from a second sensor and in response to the generated initial action, wherein the second input facilitates determining the likelihood of the event occurrence; and
based at least on the first and second inputs, automatically generate a remedial action to mitigate an effect of the event occurrence.

23. The system of claim 22 wherein automatically generating a remedial action is performed in real-time.

24. The system of claim 22 wherein the first sensor includes a first set of sensors and the second sensor includes a second set of sensors in communication with the first set of sensors.

25. The system of claim 22 wherein automatically generating an initial action includes activating the second sensor.

26. The system of claim 22 wherein the first input includes a concentration of at least one of sulfur dioxide ($SO_2$), sulfur trioxide ($SO_3$), organic sulfur, sulfuric acid ($H_2SO_4$), hydrogen sulfide ($H_2S$), thiol, nitric oxide (NO), nitric dioxide ($NO_2$), smog, ozone, volatile organic compound (VOC), total hydrocarbons, ammonia ($NH_3$), and/or hydrochloric acid (HCl).

27. The system of claim 22 wherein the second input includes at least one of a wind direction, a wind strength, an ambient temperature, an atmospheric pressure, a humidity, a rain index, or a heat index.

28. The system of claim 22 wherein at least one of the first or second inputs is a manual input of an odor.

29. The system of claim 22 wherein the second input is an input of a visual indication.

30. The system of claim 22 wherein the second input is an input of a hearing indication.

31. The system of claim 22 wherein the first and/or second inputs used to generate the remedial action are the result of averaging or exceeding a value multiple times.

32. A method of inhibiting an undesired event occurrence in an industrial facility, the method comprising:
operating an industrial facility using one or more operating parameters;
receiving a first input above a predetermined threshold;
automatically generating an initial action based at least in part on receiving the first input;
in response to generating the initial action, receiving a second input;
determining a likelihood of an undesirable event occurrence based at least in part on the received first and second inputs; and
causing one or more of the process parameters to update in order to inhibit the event occurrence in the industrial facility.

33. The method of claim 32 wherein updating one or more of the process parameters includes at least one of maintaining an operating process in a current state or initiating a shutdown of an operating process.

34. The method of claim 32 wherein updating one or more of the process parameters is done in real-time.

35. The method of claim 32 wherein the first input is received via a first sensor and the second input is received via a second sensor, the method further comprising:
activating a third sensor configured to generate a third input;
receiving, via the third sensor, the third input; and
updating the previously determined likelihood of the event occurrence.

36. The method of claim 35, further comprising:
based at least in part on the updated likelihood of the event occurrence, automatically generating a remedial action to mitigate the effect of the event occurrence.

37. The method of claim 32 wherein automatically generating an initial action includes activating the second sensor.

38. The method of claim 32 wherein the second input is of a process condition received from a camera system using at least one of laser, spectroscopy, or infrared analysis.

39. The method of claim 32 wherein the process parameters includes at least one of a process temperature, an equipment skin temperature, a process pressure, an opacity measurement, equipment operating status, or an oxygen concentration.

We claim:

1. A system located within an industrial facility, the system comprising:
   a first sensor in the industrial facility, wherein the first sensor is configured to measure a chemical concentration;
   a second sensor in the industrial facility, wherein the second sensor is configured to measure a wind direction; and
   a programmer in communication with the first sensor and the second sensor, wherein the programmer includes a computer-readable medium having instructions that, when executed, causes the programmer to:
   receive a first input from the first sensor;
   based at least on the first input, automatically generate an initial action to facilitate determining a likelihood of an event occurrence;
   receive a second input from the second sensor and in response to the generated initial action, wherein the second input facilitates determining the likelihood of the event occurrence; and
   based at least on the first and second inputs, automatically generate a remedial action to mitigate an effect of the event occurrence.

2. The system of claim 1 wherein automatically generating a remedial action is performed in real-time.

3. The system of claim 1 wherein the first sensor is one of a first set of sensors and the second sensor is one of a second set of sensors in communication with the first set of sensors.

4. The system of claim 1, wherein the programmer is further configured to, in response to automatically generating the initial action, activate the second sensor to generate the second input.

5. The system of claim 1 wherein the first input includes a concentration of at least one of sulfur dioxide ($SO_2$), sulfur trioxide ($SO_3$), organic sulfur, sulfuric acid ($H_2SO_4$), hydrogen sulfide ($H_2S$), thiol, nitric oxide (NO), nitric dioxide ($NO_2$), smog, ozone, volatile organic compound (VOC), total hydrocarbons, ammonia ($NH_3$), and/or hydrochloric acid (HCl).

6. The system of claim 1 wherein the second input further includes at least one of an ambient temperature, an atmospheric pressure, a humidity, a rain index, or a heat index.

7. The system of claim 1 wherein the first and/or second inputs used to generate the remedial action are the result of averaging or exceeding a value multiple times.

8. The system of claim 1, wherein the second sensor is configured to measure the wind direction and a wind speed.

9. The system of claim 1, wherein the second sensor is configured to measure the wind direction of an environmental or outdoor wind.

10. The system of claim 1, wherein the industrial facility includes a coke processing facility, a coke inventory processing facility, and/or a steel processing facility, and the remedial action to mitigate an effect of the event occurrence is done in the industrial facility.

* * * * *